(12) United States Patent
Goldschneider et al.

(10) Patent No.: US 6,749,847 B2
(45) Date of Patent: Jun. 15, 2004

(54) HYBRID CYTOKINE OF IL-7 AND β-CHAIN OF HEPATOCYTE GROWTH FACTOR

(75) Inventors: Irving Goldschneider, Avon, CT (US); Laijun Lai, Newington, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 09/823,933

(22) Filed: Mar. 30, 2001

(65) Prior Publication Data

US 2002/0058791 A1 May 16, 2002

Related U.S. Application Data

(60) Provisional application No. 60/193,273, filed on Mar. 30, 2000.

(51) Int. Cl.$^7$ .......................... A61K 38/20; C12N 5/10; C12N 15/24; C12N 15/63; C07K 14/54
(52) U.S. Cl. ...................... 424/85.2; 530/399; 530/402; 530/412; 435/69.4; 435/69.51; 435/71.1; 435/252.3; 435/254.11; 435/325; 435/471; 435/320.1
(58) Field of Search ................... 530/399, 402, 530/351, 412; 424/85.2; 435/69.51, 69.5, 69.6, 320.1, 7.1, 71.2, 471, 252.3, 254.11, 325

(56) References Cited

FOREIGN PATENT DOCUMENTS

WO  WO 95/13393 A1  5/1995

OTHER PUBLICATIONS

Lode et al., Gene Therapy With A Single Chain Interleukin 12 Fusion Protein Induces T Cell–Dependent Protective Immunity In A Syngenic Model of Murin Neuroblastoma, Proc. Natl. Acad. Sci. USA. vol. 95, Mar. 1998, pp 2475–2480.
Amoresano, et al., Structural Characterization and Independent Folding of a Chimeric Glycoprotein Comprising Granulocyte–Macrophage Colony Stimulating Factor and Erythropoietin Sequences. Glycobiology., vol. 8, No. 6, 1998 pp 779–790.
Rock et al., Overexpression and Structure–Function Analysis of Bioengineered IL–2/IL–6 chimeric lymphokine. Protein Engineering, vol. 5, No. 6, Sep. 6, 1992, pp 583–591.
von Freeden–Jeffrey et al., Lumphopenia in Interleukin (IL)–7 Gene–deleted Mice Identifieds IL–7 as a Nonredundant Cytokine,J. Exp. Med. vol. 181, Apr. 1995, pp 1519–1526.
Pribyl et al., Interleukin 7 Independent Development of Human B Cells, Proc. Natl. Acad. Sci. USA, vol. 93, Sep. 1996, pp. 10348–10353.
Nakamura et al., Molecular Cloning and Expression of Human Hepatocyte Growth Factor, Nature vol. 342, Nov. 23, 1989, pp. 440–443.
Rubin et al., Hepatocyte Growth Factor/Scatter Factor And Its Receptor, the c–met Proto–Oncogene Product, Biochimica et Biophysica Acta, 1993 pp. 357–371.
Zarnegar et al., The Many Faces of Hepatocyte Growth Factor: from Hepatopoiesis to Hematopiesis, J Cell Biology, vol. 129, 1995, pp. 1177–1180.
Liu et al., Molecular Cloning and Characterization of cDNA Encoding Mouse Hepatocyte Growth Factor, Biochimica et Biophysica Acta, 1216, 1993, pp. 299–303.
Oritani et al., Identification of Stromal Cell Products That interact With Pre–B Cells, J Cell Biology, vol. 134, No. 3, Aug. 1996, pp. 771–782.
Billips et al, Differential Roles of Stromal Cells, Interleukin–7, and kit–Ligand In the Regulation of B Lymphopoiesis, Blood, vol. 79, No. 5, Mar. 1, 1992, pp 1185–1192.
Hayashi et al., A Selective Culture System For Generating Terminal Deoxynucleotidyl Transferawe–Positive (TdT+) Lymphoid Precursor Cells In Vitro,J. Exp. Med. vol. 160, Dec. 1985, pp. 1622–1639.
Hayashi et al., Stepwise Progression of B Lineage Differentiation Supported By Interleukin 7 and Other Stromal Cell Molecules, J. Exp. Med. Vol 171, May 1990, pp 1683–1695.
Hardy et al., Resolution and Characterization of Pro–B and Pre–Pro–B Cell Stages in Normal Mouse Bone Marrow, J. Exp. Med. vol. 173, May 1991, pp 1213–1225 Lab Vision Corporation, TdT (Terminal Deoxynucleotidyl Transferase) Ab–1 (Clone DT01) Mouse Monoclonal Antibody, Data Sheet Rev 120600B.

*Primary Examiner*—Prema Mertz
(74) *Attorney, Agent, or Firm*—McCarter & English

(57) ABSTRACT

A hybrid cytokine comprising the B-chain of hepatocyte growth factor and IL-7, linked by a linker molecule, having pre-pro-B growth stimulating activity.

12 Claims, 26 Drawing Sheets

PPBSF cofactor:        V V N G I P T Q T N I G W M V S L

Mouse HGF β chain:     V V N G I P T Q T T V G W M V S L

Rat HGF β chain:       V V N G I P T Q T T V G W M V S L

Human HGF β chain:     V V N G I P T R T N I G W M V S L

FIG. 13

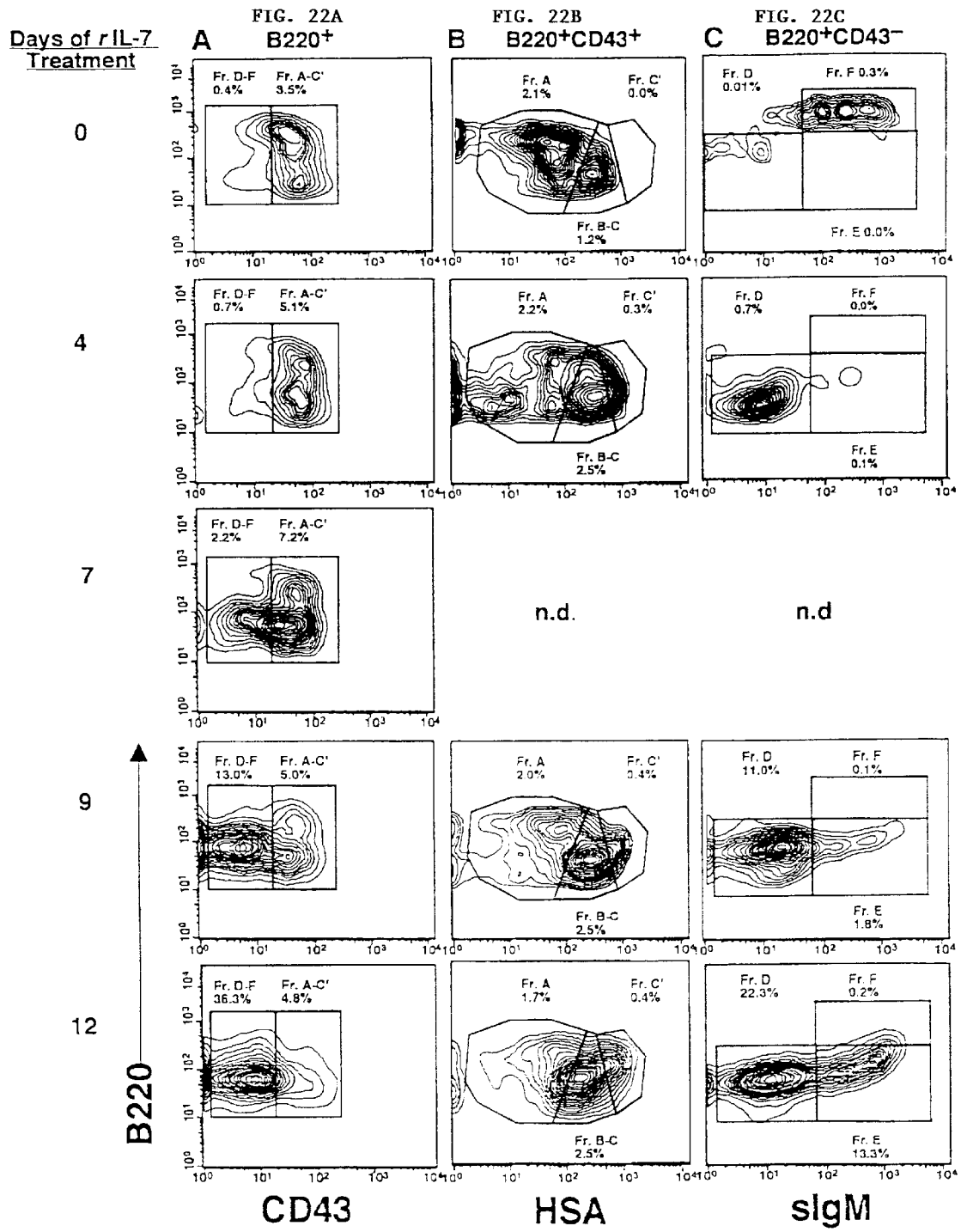

SEQUENCE LISTING

<160> NUMBER OF SEQ ID NOS: 4

<210> SEQ ID NO 1
<211> LENGTH: 18
<212> TYPE: DNA
<213> ORGANISM: Unknown
<220> FEATURE:
<223> OTHER INFORMATION: mouse HGF primer
<221> NAME/KEY: primer_bind
<222> LOCATION: (1)..(18)
<223> OTHER INFORMATION: HGF Primer 5' flanking region

<400> SEQUENCE: 1
cagtctgctc gaactgca                                              18

<210> SEQ ID NO 2
<211> LENGTH: 18
<212> TYPE: DNA
<213> ORGANISM: Unknown
<220> FEATURE:
<223> OTHER INFORMATION: mouse HGF primer
<221> NAME/KEY: primer_bind
<222> LOCATION: (1)..(18)
<223> OTHER INFORMATION: HGF primer

<400> SEQUENCE: 2

```
tggcctcttc tatggcta                                                      18

<210> SEQ ID NO 3
<211> LENGTH: 17
<212> TYPE: PRT
<213> ORGANISM: Unknown
<220> FEATURE:
<223> OTHER INFORMATION: PPBSF cofactor
<221> NAME/KEY: PEPTIDE
<222> LOCATION: (1)..(17)
<223> OTHER INFORMATION: PPBSF cofactor

<400> SEQUENCE: 3

Val Val Asn Gly Ile Pro Thr Gln Thr Asn Ile Gly Trp Met Val Ser
1               5                   10                  15

Leu

<210> SEQ ID NO 4
<211> LENGTH: 17
<212> TYPE: PRT
<213> ORGANISM: Unknown
<220> FEATURE:
<223> OTHER INFORMATION: mouse HGF beta-chain
<221> NAME/KEY: PEPTIDE
<222> LOCATION: (1)..(17)
<223> OTHER INFORMATION: Mouse HGF-Beta chain

<400> SEQUENCE: 4

Val Val Asn Gly Ile Pro Thr Gln Thr Thr Val Gly Trp Met Val Ser
1               5                   10                  15

Leu
```

HYBRID CYTOKINE OF IL-7 AND β-CHAIN OF HEPATOCYTE GROWTH FACTOR

RELATED ART

This application claims priority from U.S. Provisional Patent Application No. 60/193,273, filed on Mar. 30, 2000, now abandoned, the disclosure of which is incorporated by reference in its entirety herein to the extent permitted by the laws of the nation in which a patent is sought.

FIELD OF INVENTION

The present invention relates to the discovery of a novel IL-7/HGFβ hybrid cytokine complex referred herein as a pre-pro-B Cell Growth Stimulating Factor, or PPBSF, and methods for its production from recombinant or naturally-derived IL-7 and HGFβ.

BACKGROUND OF THE RELATED ART

Hepatocyte growth factor (HGF), also called scatter factor SF, is a heparin-binding glycoprotein that is secreted as a biologically inert single chain (pro-HGF) and is converted to its bioactive form by targeted protease digestion to an active disulfide-linked heterodimer. HGF is a natural ligand for the c-MET proto-oncogene product of a novel family of heterodimeric receptor tyrosine kinases that include Ron, Sea and Sex. It is a pleiotropic factor derived from the mesenchyme that regulates epithelial, neural, endothelial, muscle and hemopoietic cell growth, motility, morphogenesis and regeneration in many tissues and organs. The importance of HGF is seen in transgenic mice homozygous for a null mutation in the HGF gene. Such mice do not survive beyond fifteen days of embryonic development.

Mature bioactive HFG is a heterodimer consisting of a 60 kD alpha and 30 kD beta chain held together by a single disulfide bond. Structure function analysis indicates that the beta chain of HGF is required for mitogenic activity, whereas the receptor-binding domain is located in the alpha chain. Its primary structure is highly conserved among mouse, rat, human and other species. The alpha chain contains a hairpin loop at its amino terminus and four unique domains known as "kringles", while its beta chain contains a serine protease-like structure. Hence, HGF is closely homologous to plasminogen, but has no known protease activity due to mutation of the catalytic site.

HGF has been reported to be sequestered in the extracellular matrix (ECM) in vitro as well as in vivo, where it is bound to cell surface heparin sulfate glycosoaminoglycans. In general, HGF mRNA is expressed in stromal cells, whereas HGF receptor expression is mainly detected in epithelial and other parenchymal cells. This pattern suggests that HGF is an important paracrine mediator of the interaction between the parenchymal and stromal components of various tissues both during fetal development and in the maintenance of homeostasis in adult tissues.

Although a great deal is known about the actions of HGF in nonhemopoietic tissues, the role of HGF in the regulation of hematopoiesis, particularly lymphopoiesis, is fragmentary. HGF has been proposed to regulate hematopoiesis in mouse fetal liver and adult bone marrow in vivo, where it apparently can substitute for the stem cell factor (SCF) and c-kit system. HGF is produced by bone marrow (BM) stromal cells and synergizes with IL-3 or GMCSF to support the growth of hemopoietic progenitor cells (HPCs) and myeloid tumor cell lines, all of which express the HGF receptor, c-MET. In the presence of erythropoietin, HGF induces the formation of colonies along the erythroid lineage, whereas in the presence of erythropoietin plus SCF, HGF supports the growth of multipotent colonies. Similarly, upregulation of the HGF receptor on primitive hematopoietic cells may be induced by IL-11; and the synergistic interaction of these two cytokines may result in in vitro colony formation by hemopoietic stem cells (HSCs). However, HGF alone does not appear to stimulate proliferation of hemopoietic precursors. The latter may be attributed to enhancement by HGF of signal transduction by lineage-specific cytokines.

HGF has been found to promote adhesion of HPCs to fibrinectin in vitro, and may be involved in a novel paracrine signaling pathway regulating integrin-mediated adhesion and migration of B cells in germinal centers. Messenger-RNA for c-MET has been identified in thymocytes as well as in early B-lineage cells in bone marrow. It is hypothesized that HGF may be involved in a novel paracrine signaling pathway that regulates integrin-mediated adhesion and migration of B-cells in germinal centers. Thus, HGF may be one of the long sought mediators of paracrine interactions between stromal and lymphohematopoietic cells. Furthermore, HGF seems to preferentially affect hematopoietic cells in a window of differentiation between multipotent progenitors and committed precursors. For example, the addition of HGF to fetal thymus organ cultures is known to increase the generation of mature T cells.

Interleukins are a class of proteins that induce growth and differentiation of lymphocytes and hematopoetic stem cells. One interleukin in particular, IL-7, has been demonstrated over the past decade to have an essential role in the development and differentiation of murine pre-B cells.

The nature of IL-7 involvement (if any) at earlier stages of B cell development remains controversial. While it has been proposed that IL-7 is capable of acting on primitive B220⁻ B cell progenitors in the presence of stem cell factor (SCF), most investigators have concluded that the principle B-lineage targets for IL-7 are pro-B cells and pre-B cells. The pre-B cells that do appear in IL-7 KO mice are abnormal as evidenced by their failure to up-regulate or express IL-7Rα, TdT and Cμ. However, some redundancy may exist between the activities of IL-3, TSLP, and IL-7. Additionally, it has been suggested that the short-term maintenance of pre-pro-B cells, but not pro-B cells, depends on contact-mediated signals from BM stromal cells. Thus, in vivo treatment of mice with anti-IL-7 antibodies eliminates B-lineage subsets as early as the pro-B, but not the pre-pro-B, cell stage; a similar maturational arrest has been observed in mice having disrupted IL-7 receptor α-chain genes (IL-7Rα−/−); and the Tyr449 to Phe α-chain point mutation suggests that the IL-7R transmits distinct signals for cell proliferation and IgH gene rearrangement. In contrast, von Freeden-Jeffry et al. (D. Exp. Med. 181: 1519 (1995)) found that both pre-pro-B cells and pro-B cells are well represented in BM of IL-7 gene-deleted mice; and Pribyl and LeBien (Proc. Nat. Acad. Sci. USA 93: 10348 (1996)) have reported that human B-lineage cells can be generated from fetal precursors in an IL-7-independent manner.

It must be cautioned that the presence of pre-pro-B cells in IL-7Rα chain (−/−) mice does not necessarily preclude the involvement of IL-7 at this developmental stage in normal animals. An alternative explanation is that the immediate precursors of pre-pro-B cells do not require an IL-7R-mediated signal to generate pre-pro-B cells. It must also be cautioned that the presence of pro-B cells in IL-7 gene-deleted mice does not exclude a physiological role for IL-7 in early B-lineage development; neither does it preclude the possibility that cytokines other than IL-7 use the IL-7R to stimulate proliferation and differentiation of early B-lineage precursors. Indeed, our recent studies in IL-7 KO mice (see Progress Report) have demonstrated that IL-7 is essential for upregulation of TdT and IL-7R α-chain expression among early pro-B cells and for initiation of cµ expression in late pro-B cells. Therefore, while pro-B cell development occurs in IL-7 KO mice, such development is abnormal. Similar explanations may apply to conflicting reports regarding the need for IL-7 in normal human B cell ontogeny, although important species-specific differences may exist.

In prior studies, the present inventors have demonstrated that serum-free BM stromal cell conditioned medium (CM), as described in Nakumra et al., Nature 342: 440–443 (1989), Rubin et al., Biophysica Acta 1155: 357–371 (1993) and Zarnegar et al., J. Cell Biol. 129: 1177–1180 (1995), selectively stimulates the proliferation of early (TdT⁻) and late (TdT⁺) pre-pro-B cells from freshly-harvested rat BM and supports the generation (but not the proliferation) of pro-B cells. Furthermore, adsorption of CM with anti-IL-7 mAb removes this activity, whereas rIL-7 restores this activity to medium conditioned by BM stromal cells from IL-7 gene-deleted mice (−/−CM). Nonetheless, anti-IL-7 mAb is unable to neutralize the pre-pro-B cell growth-stimulating activity in IL-7 (+/+) CM or in rIL-7-supplemented (−/−) CM; and rIL-7, is unable to restore PPBSF activity to IL-7 (+/+) CM that has been adsorbed with anti-IL-7 mAb. The reason for these finding are not explained by the prior art discussed above.

SUMMARY OF INVENTION

The present inventors have discovered that the unique lymphopoietic properties of their BM lymphoid culture system was due to the presence of a self-assembling molecular complex of IL-7 and a second stromal cell-derived factor, a molecular complex previously unrecognized in the art. Biological properties of the self-assembling molecular complex, designated pre-pro-B cell growth stimulating factor, or PPBSF for short, suggest widespread medical applications.

Western blot analysis under reducing and nonreducing conditions directly demonstrates that PPBSF is a covalently-bound, Mr 55,000, heterodimer. The heterodimer comprises a non-IL-7 co-factor (coF) of about Mr 30,000 (determined using monoclonal antibodies derived from PPBSF-immunized IL-7 KO mice). PPBSF-coF has been found by the present inventors to be constitutively produced by BM stromal cells from IL-7 KO mice cultured under pro-B cell but not pre-B cell (i.e. Whitlock/Witte-type culture conditions). PPBSF has been found by the present inventors to "prime" pre-pro-B cells to proliferate in response to monomeric IL-7 in an anchorage-independent fashion by upregulating the expression of the IL-7Rα chain.

By both amino acid sequence analysis and reciprocal Western immunoblotting, it has now been discovered that the PPBSF-coF of PPBSF is the B-chain of HGF. In confirmation of the same, the bioactivity of native PPBSF has been found to be neutralized by antibodies to the HGFβ-chain. Although cDNA for pro-HGF had previously been cloned prior to the present invention, the β-chain cDNA had not been isolated and cloned into appropriate expression vectors.

PCR amplification of the coding sequence of HGF in stromal cells from IL-7 KO mice resulted in the application of two transcripts of 2230 and 840 bp. The smaller product showing complete homology with the published mouse HGFβ gene was subcloned into the mammalian expression vector pcDNA3.1 (+) and transfected into Chinese hamster ovary (CHO) cells. The HGFβ gene was also subcloned into the prokaryotic fusion protein expression vector pCAL-n and transformed into E. coli BL21 (DE3).

The rHGFβ DNA was purified by calmodulin affinity resin. Unexpectedly, rIL-7 spontaneously complexed with rHGFβ in the presence of low molecular weight heparin sulfate (HS)-derived oligosaccharides (below about 3000 kD) to form a heterodimer having the functional activity of native PPBSF. However, because several naturally occurring variant HGFβ produced by alternative splicing of the HGF gene have been identified, the precise form of HGFβ represented in PPBSF remains to be determined, as does its origins (i.e. alternative splicing or duplication of the HGF gene), synthesis, assembly with IL-7; and display.

This is the first demonstration of a naturally occurring, or an artificially constructed, hybrid cytokine (i.e. a biomolecular or unimolecular complex of the bioactive portions of two or more disparate cytokines or growth factors). It also is the first demonstration of a bioactive form of IL-7 and HGFβ that selectively supports the proliferation and subsequent differentiation of pre-pro-B cells. Although IL-7 plays an essential role in the development of early B lymphocytes, IL-7 alone doesn't support the proliferation of pre-pro-B cells. Although HGF can synergize with IL-3, GM-CSF or erythropoietin to support the growth of HPCs, myeloid cell lines, and erythroid cells, respectively, it has not been reported to play a direct role in the early B-cell development. Hence, the discovery of the IL-7/HGFβ complex not only provides a reagent that regulates the earliest stages of B-lymphocyte development in bone marrow, but it may presage the existence of a series of other naturally occurring hybrid cytokines as well as the artificial creation of hybrid cytokines with unique pharmacological properties. In addition, the existence/creation of hybrid cytokines may render pleiotropic growth factors lineage-specific, thereby directing the commitment of hemopoietic and other pluripotent stem cells to development along selective pathways.

"IL-7/HGFβ complex," as used herein, refers both to a bimolecular protein complex which features both the IL-7 (Interleukin-7) and HGFβ polypeptides, biologically-active variants thereof, and to a unimolecular protein which includes the bioactive portions of IL-7 and HGFβ connected with a flexible linker. The expression "linker" relates to linkers of any kind, which are suitable for the binding of polypeptides.

Examples of such linkers include but are not limited to a disulfide-bridge connecting amino acids from both polypeptides; heparin or heparan sulfate-derived oligosaccharides (glycosoaminoglycans) connecting both polypeptides; bifunctional or chemical cross-linkers; and a peptide or polypeptide linker. The unimolecular protein can also be a fusion polypeptide. For example, a polypeptide featuring the bioactive portions of IL-7 and HGFβ can be fused with each other, and the linker can be a disulfide-bridge produced by the two polypeptides.

PPBSF has been found to selectively stimulate the proliferation of pre-pro-B cells and to support the generation of pro-B cells (the next recognized stage in early B-lymphocyte development). PPBSF "primes" pre-pro-B cells to proliferate in response to monomeric IL-7 in an anchorage-independent fashion by upregulating the expression of the IL-7 receptor (R) α chain. PPBSF also upregulates the expression of terminal deoxynucleotidyl transferase (TdT) and initiates the expression of cytoplasmic immunoglobulin mμ heavy chain (cμ). PPBSF also stimulates the proliferation of thymocytes.

The IL-7/HGFβ complex can be isolated from natural sources, e.g., mammalian tissues or cell lines which are known to be a source of cytokines or growth factors. It may also be formed from recombinant and/or natural components as shown herein. PPBSF was shown to be expressed by bone marrow stromal cells in our pro-B cell culture system. Alternatively, PPBSF can be reconstituted from products of prokaryotic or eukaryotic expression of exogenous DNA sequences i.e., derived by recombinant means.

The present invention also includes biologically-active variants of the IL-7 or HGFβ complex. Such variants may include any homologous peptide to either IL-7 or HGFβ, for example including substitution analogs wherein one or more amino acids have been substituted with different amino acids, deletion analogs wherein one or more amino acids have been deleted, and addition analogs wherein one or more amino acids have been added. Deletions and additions of one or more amino acids are made either within an internal region of the polypeptide or at the amino or carboxyl terminal ends. Additional potential variations include other heterodimeric (or multimeric) cytokine complexes containing IL-7 and/or HGF (α and/or β chains), and other hybrid cytokines unrelated to either IL-7 or HGF, whether naturally occurring or artificially created, including those that bind to the receptors for HGF, IL-7, and/or γc.

Western immunoblotting showed that PPBSF was a covalently-linked heterodimer of IL-7 and an Mr 30,000 cofactor. Partial $NH_2$-terminal amino acid sequence analysis of purified PPBSF cofactor showed the first 15 of 17 amino acid residues were identical to the published sequence of mouse HGF β chain. Western blot analysis confirmed the identity of PPBSF cofactor as the β chain of HGF.

In conjunction with the invention, the present inventors have: (1) established a pro-B cell culture system that selectively generates large number of pre-pro-B cells and pro-B cells from rat, mouse and human bone marrow; (2) demonstrated that medium conditioned by BM stromal cells in our pro-B cell culture system selectively supports the development of pre-pro-B cells and pro-B cells in vitro; (3) demonstrated the existence in conditioned medium of a non-IL-7 component of PPBSF by anti-IL-7 antibody neutralization and adsorption experiments; (4) demonstrated that PPBSF is a covalently-linked heterodimer of IL-7 and a Mr. 30,000 cofactor by Western immunoblot analysis under reducing and non-reducing conditions; (5) demonstrated that PPBSF is a self-aggregating complex of IL-7 and a Mr. 30,000 cofactor by addition of IL-7 to conditioned medium from IL-7 gene-deleted mice; (6) demonstrated that PPBSF, but not IL-7 or PPBSF cofactor alone, upregulates the expression of IL-7Rα, TdT and cμ on/in pro-B cells from IL-7 gene-deleted mice and "primes" then to proliferate in response to monomeric IL-7; (7) developed neutralizing monoclonal antibodies specific for the PPBSF cofactor; (8) identified the PPBSF cofactor as the β chain of HGF/SF by amino acid analyses and reciprocal Western blotting; (9) cloned the HGFβ cDNA into mammalian and prokaryotic xpression vectors and expressed the protein in mammalian (CHO) and prokaryotic e. coli BL21 (DE3) cells; and (10) demonstrated that rIL-7 spontaneously complexes with r HGFβ in the presence of low molecular weight heparin sulfate (HS)-derived oligosaccharides to form a heterodimer having the functional activity of native PPBSF.

BRIEF DESCRIPTION OF THE FIGURES

The accompanying figures, which are incorporated in and constitute part of the specification, illustrate presently preferred embodiments of the invention, and together with the general description given above and the detailed description of the preferred embodiments given below, serve to explain the principles of the invention.

FIG. 13 is a partial NH2-terminal amino acid sequence identity of purified mouse PPBSF cofactor, and its comparison with the published sequence for the HGF β chain in mouse;

FIG. 22 are a series of flow cytometry histograms of B-cell populations demonstrating the effect of in vivo injection of rIL-7 into IL-7 KO mice on the development of B-lineage cells in BM. IL-7 KO mice were injected i.p. with 40 ng rIL-7 daily for 4, 7, 9, or 12 days. BM cells were harvested on day 0 or 1 day after the end of each series of injections, and were subjected to FCM analysis. (A) The B220$^+$ population was subdivided into CD43$^+$ (Fr. A-C') and CD43$^-$ (Fr. D-F) cells according to relative fluorescence intensity. (B) The B220$^+$ CD43$^+$ population was subdivided into Fr. A, B-C and C' according to relative fluorescence intensity for HSA. (C) The B220$^+$ CD43$^-$ population was separated into Fr. D, E and F according to relative fluorescence intensity for sIgM. The relative numbers of cells in each of these fractions is expressed as the percentage of total nucleated BM cells per femur. (n.d.=not determined).

DETAILED DESCRIPTION OF INVENTION

Figure 1:
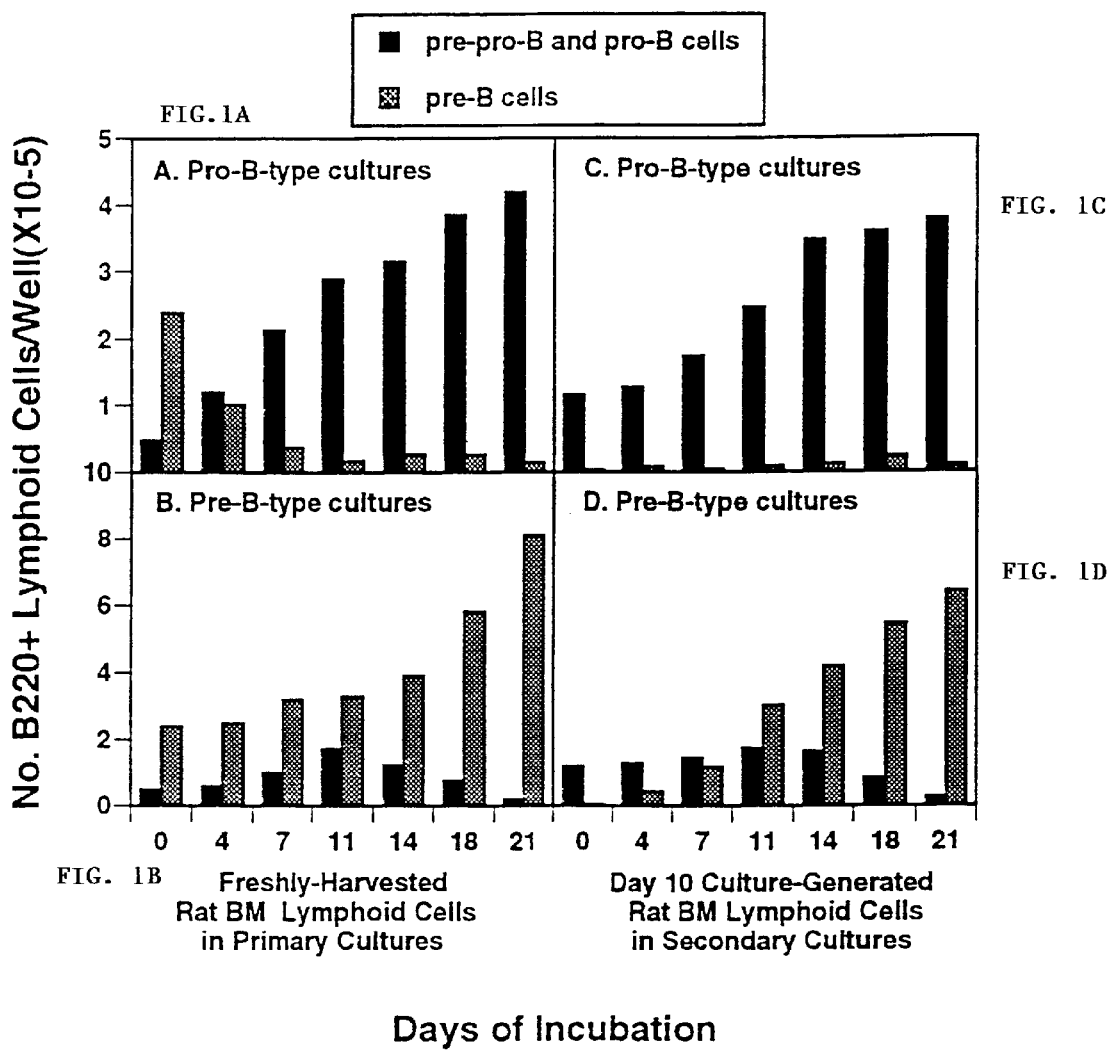
FIG. 1A–FIG. 1D are bar graphs of the number of pre-pro-B and pro-B cells versus pre-B cells derived from rat bone marrow lymphoid cells grown in a pro-B type culture as described (FIGS. 1A and 1C) and pre-B type culture (Whitlock/Witte) (FIGS. 1B and 1D) over a twenty-one day period emanating from either freshly-harvested cells in primary culture (FIGS. 1A and 1B) or emanating from day 10 culture-generated rat bone marrow lymphoid cells in secondary culture (FIGS. 1C and 1D)

Considerable progress has been made using long-term adherent cell-dependent culture systems to identify stromal cell-derived cytokines that regulate pro-B and pre-B cell development in bone marrow. However, much less is known about the factors that regulate pre-pro-B cell development. To approach this problem, the present inventors developed a long-term lymphoid BM culture system (LTBMC) (as described in Nakumra et al., Nature 342: 440–443 (1989), Rubin et al., Biophysica Acta 1155: 357–371 (1993) and Zamegar et al., J. Cell Biol. 129: 1177–1180 (1995)) that selectively supports the proliferation, self-replication and differentiation of pre-pro-B cells from rat, mouse and human BM. Using this culture system, the present inventors have identified, affinity-purified, and raised monoclonal antibodies to a novel IL-7-associated growth factor that selectively stimulates proliferation of pre-pro-B cells and supports their differentiation to pro-B cells. As revealed by Western blot analysis, amino acid sequencing and molecular cloning, this pre-pro-B cell growth stimulating factor, is a covalently-bound heterodimer of IL-7 and the β-chain of hepatocyte growth factor (HGF).

The 30 kDa, non-IL-7 component of the PPBSF heterodimer (PPBSF-coF) is disclosed herein as the β-chain of the hepatocytic growth factor/scatter factor (HGF/SF). In addition, it is demonstrated herein that active artificially-derived PPBSF can be produced by combining purified HGFβ, made by the cloning of the coding sequence of HGFβ, with rIL-7, in particular in the presence of low molecular weight heparin sulfate. This is a remarkable and wholly unexpected finding, inasmuch as HGF (of which the β-chain is the mitogenic component) is one of the most important cytokines involved in the regulation of organogenesis in embryonic life and of tissue regeneration and repair in adult life.

To the inventors' knowledge, this is the first demonstration of any hybrid cytokine (possibly aside from IL-12, which is structurally analogous to a disulfide-linked secreted complex of a cytokine with a cytokine receptor), and suggests a new paradigm by which pleiotropic cytokines (in this case HGF) can be rendered organ, tissue, lineage or stage-specific; and by which the functions of organ, tissue, lineage or stage-specific cytokines (in this case, IL-7) can be enhanced or altered. It also suggests a paradigm by which commitment of hemopoietic stem cells to development along a particular cell lineage may be regulated by such hybrid cytokines.

Further insights into the probable actions of PPBSF in regulating normal pre-pro-B cell and pro-B cell development in vivo and in vitro have been gained by the present invention. Thus, PPBSF, but not monomeric IL-7, appears to induce pre-pro-B cells and/or pro-B cells to upregulate TdT and IL-7Rα and to initiate synthesis of $c\mu$. Subsequently, monomeric IL-7 can stimulate these "primed" pro-B cells to proliferate and generate pre-B cells.

Much of what is known about the microenvironmental regulation of early B cell development stems from the use of long-term in vitro bone marrow culture systems. As discussed above, the present inventors have previously described a long-term lymphoid cell culture system that selectively generates large numbers of pre-pro-B cells and pro-B cells from rat, mouse, and human BM in the presence of mouse BM adherent cells (Nakamura et al., *Nature* 342: 440–443, 1989; Rubin J S et al. *Biophysica Acta* 1155: 357–371, 1993; Zarnegar R et al.1995; *J Cell Biol* 129: 1177–1180; and Liu et al. *Biophysica Acta* 1216: 299–303) referenced herein as the pro-B cell culture. Approximately 50% of the lymphoid cells show partial D-J heavy chain Ig gene rearrangements; whereas the remaining lymphoid cells have a germline configuration, and are themselves derived from even more primitive, B220⁻, precursors. Unlike more traditional LTBMC systems, the pro-B cell culture system, so described, selectively generates pre-pro-B cells and early pro-B cells from adult BM, even when the lymphoid progenitors are separated from the adherent cell layer by a microporous membrane culture insert or cultured in stromal cell conditioned medium (CM). However, under optimal conditions, the "early" (TdT⁻) pre-pro-B cells, adhere tightly to BM stromal cells, and self-replication occurs indefinitely upon serial transfer to new adherent cell layers in vitro. In addition, these pre-pro-B cells produce non-adherent pro-B cells in vitro and rapidly generate sIgM$^{30}$ B cells after in vivo transfer. Yet, neither $c\mu^+$ pre-B cells nor sIgM$^{30}$ B cells are produced in significant numbers in vitro, even in the presence of 2-ME.

Although there is no evidence of progressive clonal restriction or leukemic transformation under normal circumstances, the pro-B cell culture system is also able to generate leukemic pre-pro-B cells and pro-B cells in vitro, when seeded with BM cells from rats that have been infected neonatally with the Gross leukemia virus or from human patients with acute lymphoblastic leukemia (ALL). Like their normal counterparts, these B-cell lineage leukemias are dependent upon the presence of a BM adherent cell layer (or conditioned medium therefrom). Moreover, the cells that undergo leukemic transformation co-isolate on the FACS with the precursors that generate normal pro-B cells. They therefore have proved useful as target cells in bioassays for stage specific lymphoid growth-stimulating factors.

The demonstration herein that PPBSF is a heterodimer of IL-7 and the HFGβ-chain may provide key insights into the mechanisms by which the earliest stages of lymphoid commitment and/or expansion from HSCs in BM are regulated.

It is unclear as to why a hybrid cytokine, in which IL-7 substitutes for the α-chain of HFG, selectively supports the proliferation and differentiation of pre-pro-B cells in vitro. The present inventors have hypothesized, but the invention is not limited by such hypothesis, that evolutionarily such activity occurred to address: 1) the need for cognate interactions between pre-pro-B cells and BM stromal cells for optimal lymphopoiesis; 2) the need for self-replication of pre-pro-B cells to maintain the precursor cell pool; 3) the expression of only low levels of high affinity IL-7R. PPBSF can satisfy all of these requirements by stimulating the self-replication of pre-pro-B cells, by functioning primarily as a cell surface (or ECM)-bound molecular complex; and by upregulating IL-7Rα-chain expression. Such a role for PPBSF in normal BM provides additional insights into the nature of the cognitive interactions between pre-pro-B cells, BM stromal cells and associated ECM.

Inasmuch as both IL-7 and HGF are avidly-bound by heparin, and are shown herein to be functionally cross-linked by low molecular weight (below about 3000 kD) heparin-sulfate-derived oligosaccharides, it is possible that PPBSF is a component of the stromal cell-associated extracellular matrix that characterizes the culture system. Despite the inability to detect PPBSF activity in extracellular matrix extracted from BM adherent cell layers with hypetronic saline, continued efforts are warranted based on recent reports of the regulation of growth factor signaling by ECM proteins, and especially the description by Oritani and Kincade (J. Cell. Biol. 134: 771–782) of a series of ECM glycoproteins that selectively increase the IL-7-dependent proliferation of pre-B cells.

The sequential expression of low and high concentrations of high affinity IL-7R during early B-lineage development is analogous to events observed during early thymocyte development. Given that pro-B cells from γc gene-deleted mice express only low levels of IL-7R α-chain, IL-7Rα KO mice apparently fail to generate pro-B cells, and excess IL-7 fails to increase pre-pro-B cell generation in vivo, it is possible that signal transduction through high affinity IL-7R (α/γc) is required to transmit a proliferative signal for pre-pro-B as well as pro-B cells. This is further supported by the inventors' recent observation that, although the IL-7Rα is not upregulated on pro-B cells from IL-7 (−/−) mice, its expression can be induced on such cells in vitro by purified PPBSF, but not rIL-7. Hence, PPBSF may favor the association of IL-7Rα and γc chains under conditions of low IL-7Rα expression, whereas monomeric IL-7 may require high concentrations of IL-7Rα.

There appears to be a "priming" effect of PPBSF for monomeric IL-7, wherein PPBSF selectively regulates the $G_1/S$ transition of pre-pro-B cells, and monomeric IL-7 selectively regulates the $G_1/S$ transition of pro-B cells. Such sequential actions of PPBSF and monomeric IL-7 would correlate nicely with the demonstration of separate microanatomical niches, differential adhesion mechanisms, decreasing need for cognitive interactions, and increasing dependency on IL-7 during early B cell development. Compatible conclusions have been reached by Billips et al (Blood 79: 1185 (1992)) using the S17 stomal cell line; and Hayashi et al. (J. Exp. Med. 171: 1683 (1990)), using the PA6 stromal cell line. Even more intriguing is the possibility that PPBSF may be involved in regulating the commitment of HSC to development along the B (and possibly T) lymphoid pathways. Hence, differences in molecular form and, possibly, site of expression may render IL-7 pre-pro-B cell stage-specific; and differences in the receptor-binding domain (IL-7 for HGFα) may render HGFβ lymphoid lineage-specific.

Despite the occurrence of early B-lineage development in IL-7 KO and IL-7R KO mice, the present inventors postulate that IL-7, in the form of PPBSF, is the preferred ligand under physiological conditions. Furthermore, the present inventors suspect that those compensatory mechanisms that do exist may be suboptimal, given that pro-B cells in IL-7 (−/−) mice do not upregulate TdT or IL-7Rα during IgH gene rearrangement, do not initiate cμ expression, and do not proliferate in response to monomeric IL-7. However, once stimulated with PPBSF, TdT and IL-7Rα are upregulated, cell proliferation is stimulated by monomeric IL-7, and cμ is expressed, at least in vitro. These results may help to explain why the in vivo administration of anti-IL-7 mAb prevents the development of pro-B cells in normal mice, namely by causing the coordinate elimination of IL-7 and PPBSF.

The present inventors have: 1) defined the microenvironmental anatomy for the contact-dependent phase of pre-pro-B cell and pro-B cell development; 2) traced the parent-progeny relationships of "early" and "late" pre-pro B cells and pro-B cells; and 3) identified a novel 55 kD IL-7-associated heterodimer that appears to regulate the proliferation of pre-pro-B cells, their differentiation to pro-B cells, and their ability to respond to monomeric IL-7 in a contact-independent manner. In addition, they have utilized the IL-7 KO mouse to isolate, purify, and raise monoclonal antibodies to a 30 kD cofactor that spontaneously complexes with IL-7 to form the claimed pre-pro-B cell growth-stimulating factor (PPBSF). The PPBSF-coF is identified by the present inventors as the HGFβ-chain. The present inventors have generated the PPBSF in recombinant form.

Applications

As would be understood by one of ordinary skill in the art, PPBSF could be used alone or in conjunction with other factors to treat a number of hematopoietic disorders in human beings and/or domesticated animals that result from disease or injury to B-lineage (and other) cells in bone marrow. These include the following: pancytopenia, myelodysplastic syndrome, leukemias and lymphomas, hereditary or acquired immunodeficiency disorders, and myelosuppression resulting from radiation treatment, chemotherapy, drug allergies, or environmental toxins. PPBSF may also be useful in expanding and/or enhancing engraftment of B-lineage progenitor cells in vivo syngeneic, allogeneic or autologous bone marrow transplantation, or ex vivo in marrow or HSC cultures prior to transplantation. Further, it would be expected that such treatment will reduce the period of depressed immunity due to delayed B cell regeneration that frequently is experienced by patients after transplantation. Also, PPBSF may enhance the engraftment of genomically modified B-cell precursors in the treatment of selected immunodeficiency and leukemic disorders. In addition, PPBSF may be used to enhance the growth of leukemic B-lineage cells in vitro to permit customized screening profiles of chemotherapeutic and immunotherapeutic sensitivity to be developed for individual patients, or to permit individualized tumor vaccines to be produced. Furthermore, a deficiency or abnormality of PPBSF itself may prove to be a cause of immunodeficiency in some patients, making screening assays for PPBSF useful.

In bone marrow transplantation, the PPBSF may be used to pretreat the marrow prior to transplantation and/or may be administered in vivo after transplantation. The PPBSF may be used as a pharmacological agent itself or introduced by way of a transformed cell, viral vector, etc. PPBSF proffers significant therapeutic advantages to the bone marrow recipients in that it substantially increases lymphocyte precursors. Bone marrow recipients usually take months to approach normal levels of B and T-lymphocytes after transplantation. PPBSF has been seen not only to stimulate parental cells to generate large numbers of mature progeny, but to produce more parental cells (self-replication), leading to long-term engraftment.

Animal studies suggest that the hybrid cytokine of the present invention may have particularly usefulness in the treatment of acute lymphoblastic leukemia in that it has been found to proliferate leukemic as well as normal cells. By administering PPBSF to leukemic patients the malignant cells can be activated to proliferate. As most chemotherapeutic agents today are designed to selectively kill dividing cells, such chemotherapeutic agents in conjunction with PPBSF provide a better "kill rate" of the malignant cells (a certain portion of the population of malignant cells usually are non-dividing at time of chemotherapy and therefore are protected from the cytotoxic effect of the chemotherapeutic agents).

Inasmuch as well as PPBSF also stimulates proliferation of immature thymocytes, it may prove to be equally useful in treating disorders of T lymphocytes as well as B lymphocytes. Indeed, should PPBSF induce commitment of HSC to bipotential lymphoid differentiation, it could be used to correct severe combined immunodeficiency disorders, possibly including AIDS.

PPBSF can also be used in vitro to screen the blood and other tissues of patients treated with chemotherapy to determine whether malignant lymphocytes still exist, that is, by increasing the pool of malignant lymphocytes in a sample allowing for easier detection of the same. PPBSF may also be used to establish cultures of leukemic cells from individuals which may be used in screening assays for panels of chemotherapeutic agents. An additional potential use of hybrid cytokines, containing HGFβ or other pleiotropic growth factors complexed with organ, tissue, lineage or stage-specific cytokines, is to direct the differentiation of embryonic stem cells along specific pathways in vitro for organ, tissue or cell transplantation purposes and/or to induce regeneration of damaged organs, tissues or cell lineages in vivo.

The ability of the pro-B cell culture previously described by the present inventors' (see above) to sustain leukemic pre-pro-B cells and pro-B cells from the BM of human patients with acute lymphoblastic leukemia suggests that the growth of these cells may also be regulated, at least in part, by PPBSF. Abnormalities in pro-B cell development can also be reproduced in cultures of BM cells from several murine models of autoimmunity and immunodeficiency. The ability to selectively generate pre-pro-B cells in vitro provides a unique opportunity to determine the nature of the microenvironmental cells and factors that regulate normal and abnormal lymphopoiesis at this critical stage of development.

Now turning to the figures, there is shown particular compositions and methods within the scope of the present invention. Such figures, and examples associated therewith, are presented in order to make certain aspects of the present invention more clearly understood and are not intended to limit the scope of the invention described herein in any manner.

EXAMPLE 1

Growth of Pre-Pro-B, Pro-B and Pre-B Cell Compartments on Different Culture Media As illustrated in FIGS. 1A and 1B, after inoculation with freshly-harvested BM cells the pre-pro-B cell and pro-B cell compartments in the pro-B cell culture previously described by the inventors (Hayashi, et al, J. Exp. Med. 160: 1622–1639 (1984)) progressively expands with time, whereas the pre-B cell compartment progressively contracts. In contrast, under Whitlock/Witte-type culture conditions, the pre-B cell compartment progressively expands with time (FIGS. 1C and 1D) whereas the pre-pro-B cell and pro-B cell compartments progressively contract (after a brief period of expansion). Furthermore, pre-pro-B cells and pro-B cells from the lymphoid culture system generate pre-B cells when placed in Whitlock/Witte cultures or CM therefrom.

EXAMPLE 2

Recreation of Bone Marrow Microenvironment for Early Lymphopoiesis In Vitro

The nature of the interactions between BM lymphoid precursor cells and BM adherent microenvironmental cells was investigated by a combination of immunophenotyping and scanning and transmission electron microscopy of primary cultures.

The results of such studies show that two distinct microenvironmental regions are represented within the BM adherent cell layer: (a) paucilayer (PL) regions, composed of two or three horizontally oriented layers of stromal cells; and (b) multilayer (ML) regions, containing 4 to 8 layers of stromal cells. In both regions, proliferating lymphoid cells expressing the B220, and/or heat stable antigen (HSA) early B-lineage antigens, are "sandwiched" between adjacent layers of stromal cells and enveloped by cytoplasmic processes from interdigitating mouse macrophages (pseudoemperipolesis). Small clusters containing 5 to 50 lymphoid cells, preferentially develop in the PL regions are comprised primarily of TdT cells that can generate $TdT^+$ cells upon transfer onto fresh adherent cells layers.

Under ideal conditions, individual clusters are clonally derived and the seeding efficiency of the culture system approaches 100%. Large clusters, containing up to 1,000 lymphoid cells, preferentially develop in the ML regions and are comprised primarily of $TdT^+$ cells. The ML regions bear a close resemblance to the recently described pro-B cell-enriched, multi-cellular aggregate fraction of freshly harvested mouse BM. Hence, this system appears to structurally recreate in vitro the in vivo microenvironment for the development of pre-pro-B cells and pro-B cells.

EXAMPLE 3

Figure 2:
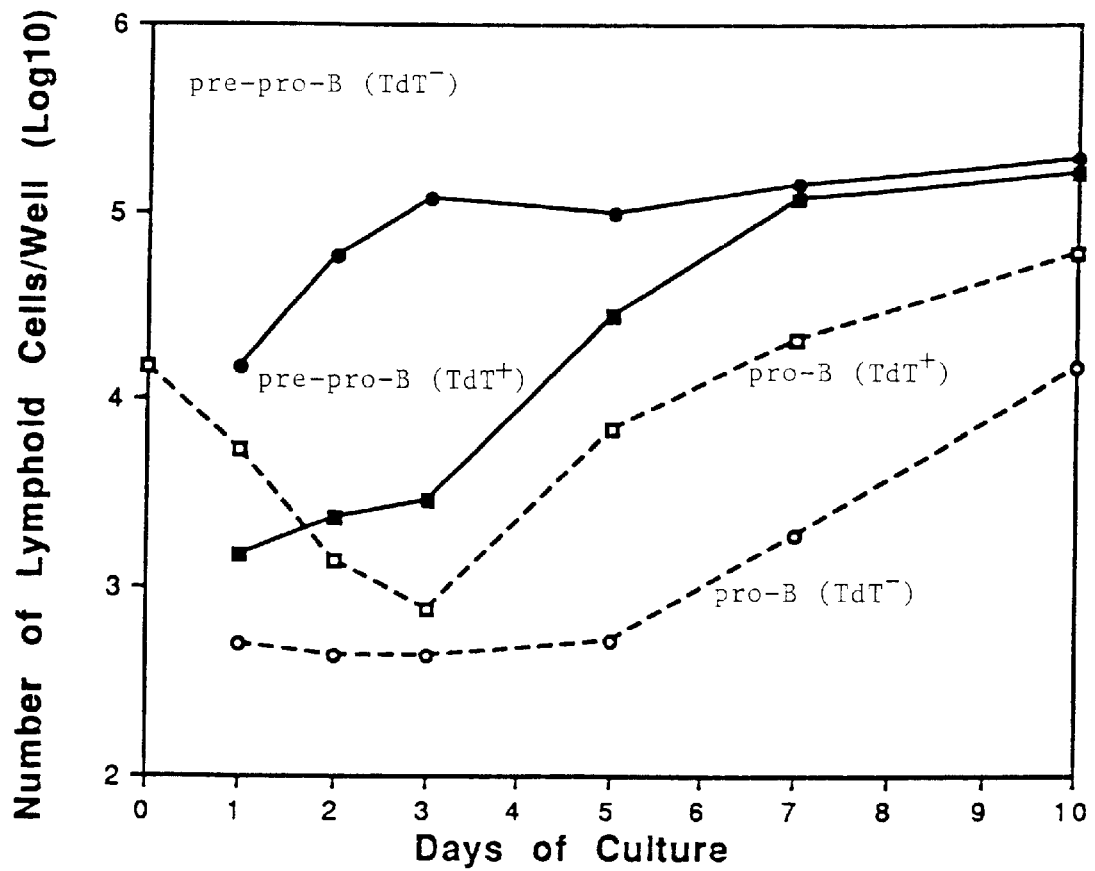
FIG. 2 is a graph of the sequential proliferation and differentiation of four subsets of B-cell progenitors, pre-pro-B (TdT$^-$), pre-pro-B (TdT$^+$), pro-B (TdT$^+$) and pro-B (TdT$^-$), cultured in the pro-B culture system as described, over ten (10) days of culture.

Properties and Developmental Relationships of the Lymphoid Cells in the Adherent and Nonadherent Compartments of the Pro-B Culture System Turning to FIG. 2, four sequentially appearing subsets of B-cell progenitors in the inventors' pro-B culture system were characterized. The first lymphoid subset consists of adherent $TdT^-$; (early) pre-pro-B cells that reach plateau numbers on day 3; and the second subset consists of adherent TdT+-(late) pre-pro-B cells that plateau on day 7. This is closely followed by a parallel increase in the number of TdT+ (early) and TdT– (late) pro-B cells in the non-adherent phase.

Figure 3:
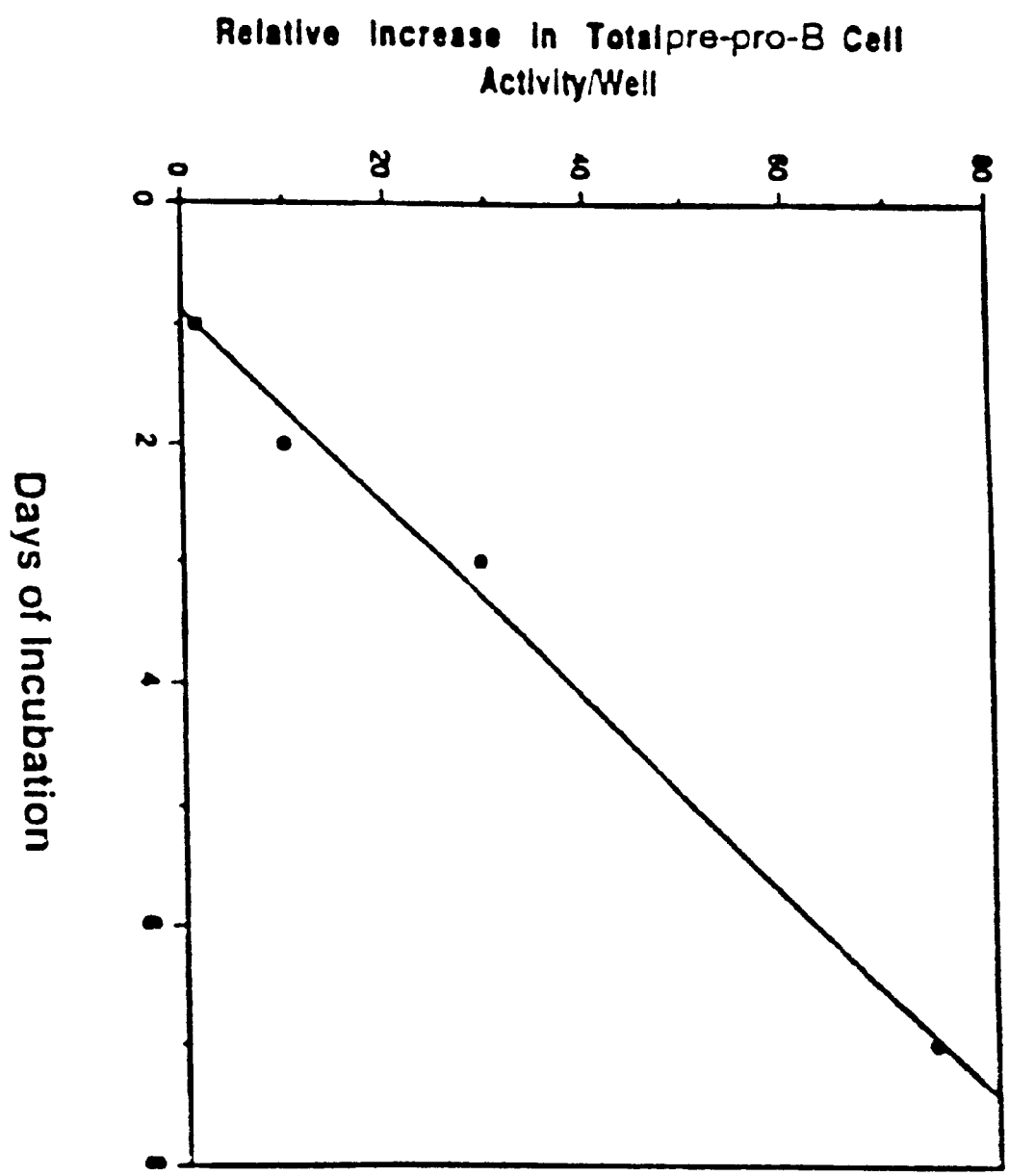
FIG. 3 is a graph illustrating the relative increase in total pre-pro-B cells freshly harvested from rat bone marrow cultured over an eight (8) day period.

In vitro transfer experiments demonstrated that virtually all of the early pre-pro-B cells in freshly harvested rat BM adhere to the mouse BM stromal cells during the first 24 hrs of culture; and by day 7 of culture, these cells had increased more than 20-fold on a per cell basis and more than 70-fold on a per well basis (FIG. 3). It was also observed that a decrease in the concentration of fetal bovine serum in the culture medium resulted in the selective release of late, but not early, pre-pro-B cells into the non-adherent compartment. These studies indicate that a stepwise progression of the earliest detectable stages in lymphoid development was associated with changes in stromal/lymphoid cell interactions partly regulated by serum-dependent adhesion mechanisms.

EXAMPLE 4

Figure 4:
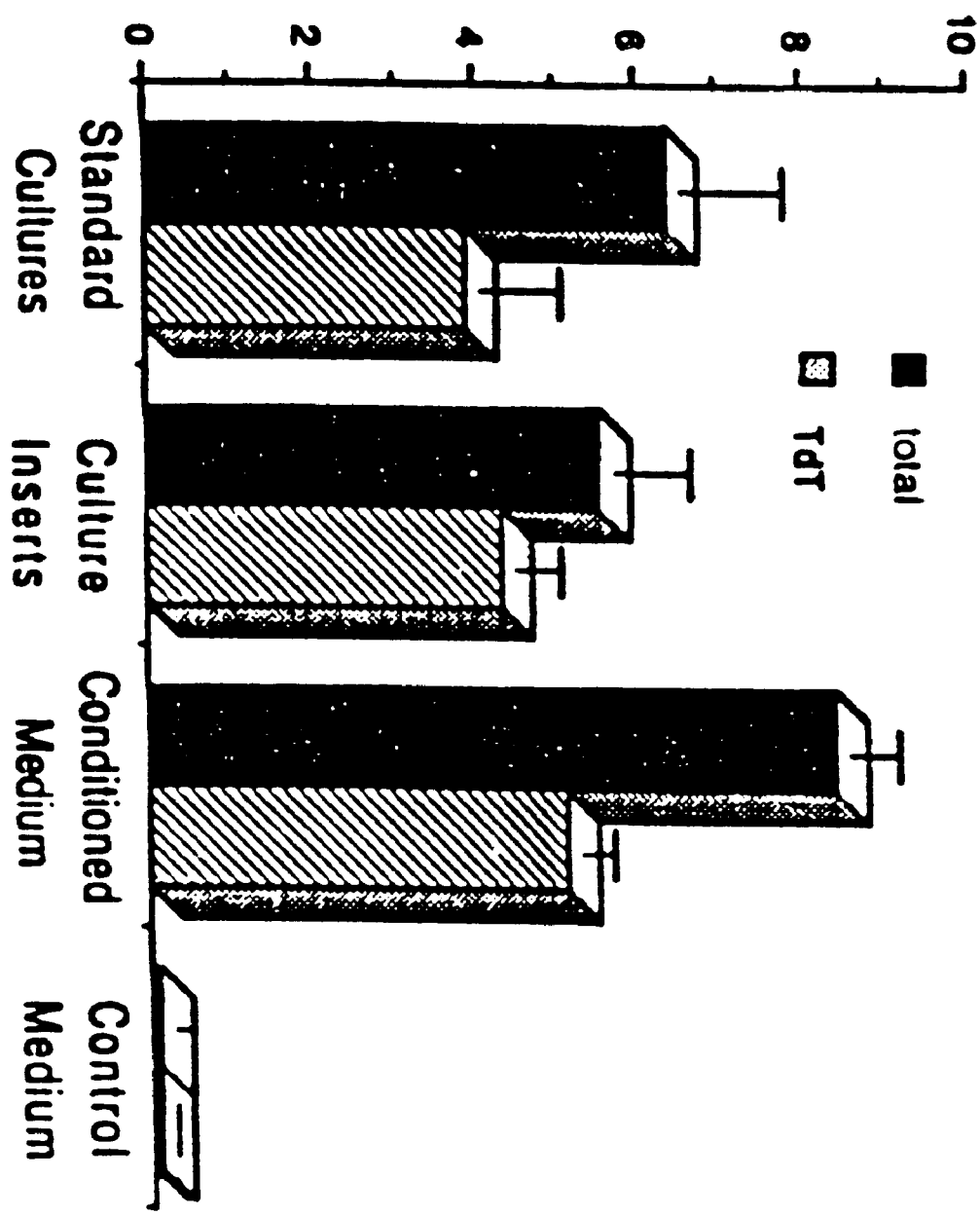
FIG. 4 is a bar graph of growth of rat bone marrow lymphoid cells in different media, total as well as those displaying the TdT marker.

Ability of Medium Conditioned by BM Stromal Cells to Selectively Support the Development of Pre-Pro-B Cells and Pro-B Cells in Vitro Although the pro-B culture system is characterized by physical interaction-between developing lymphocytes, BM stromal cells and macrophages, experiments using microporous membrane culture inserts demonstrate that these cognitive recognition events, albeit more efficient, are not essential (FIG. 4). Similarly, medium conditioned (CM) with mouse BM adherent cells supported the proliferation of lymphoid precursor cells in a dose-dependent manner. Upon ultrafiltration, all of the lymphostimulatory activity in the CM was recovered in the 50–100 kD apparent MW fraction; and double immunofluorescence for incorporated bromodeoxyuridine (BrdU) and early B-lineage markers indicated that the lymphoproliferative response selectively involved early ($TdT^-$) and late ($TdT^+$) pre-pro-B cells, but not pro-B cells.

EXAMPLE 5

The Pre-pro-B Cell Growth-Stimulating Factor (PPBSF)

Detection of IL-7 and a non-IL-7 Components of PPBSF

Figures 5A, 5B:
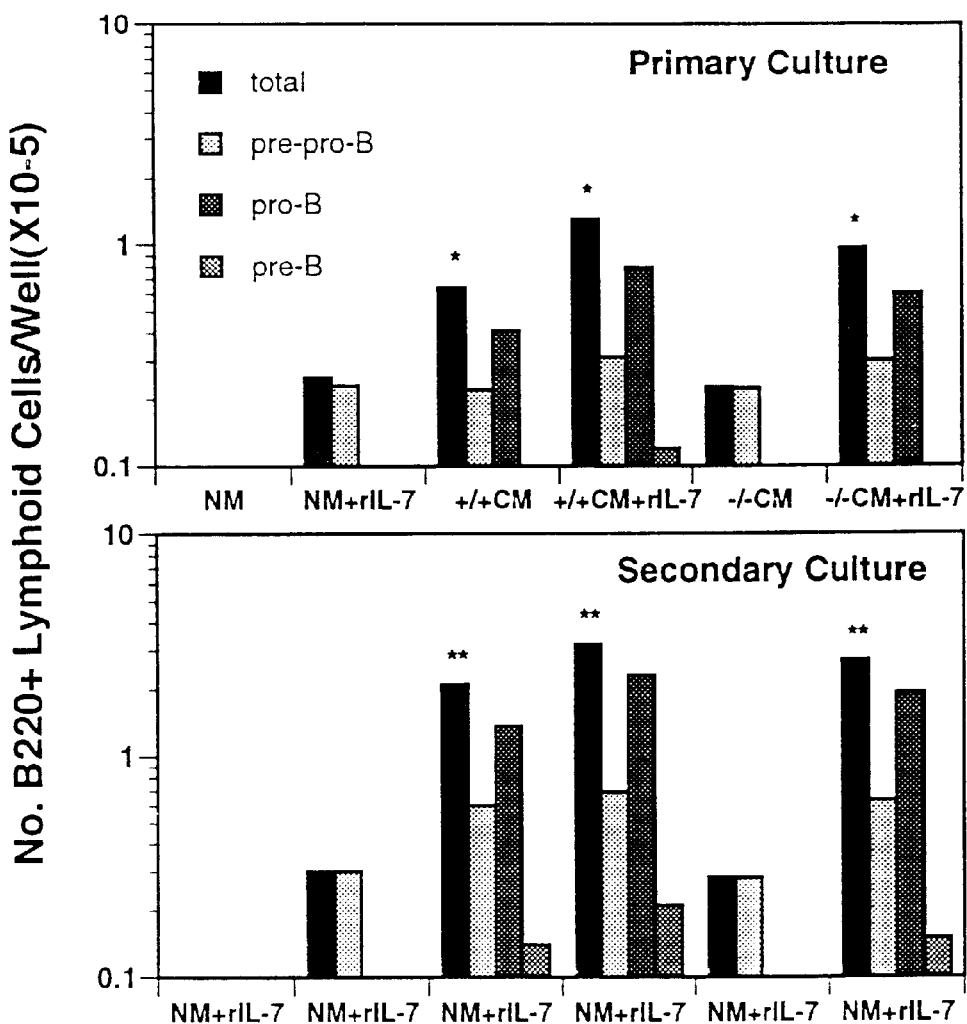
FIGS. 5A and 5B are bar graphs of the number of cells (total, pre-pro-B, pro-B, and pre-B) found in primary culture (FIG. 5A) and secondary culture (FIG. 5B) given different combinations of normal medium (NM), bone marrow stromal conditioned medium (CM), and/or rIL-7.
Figure 6:
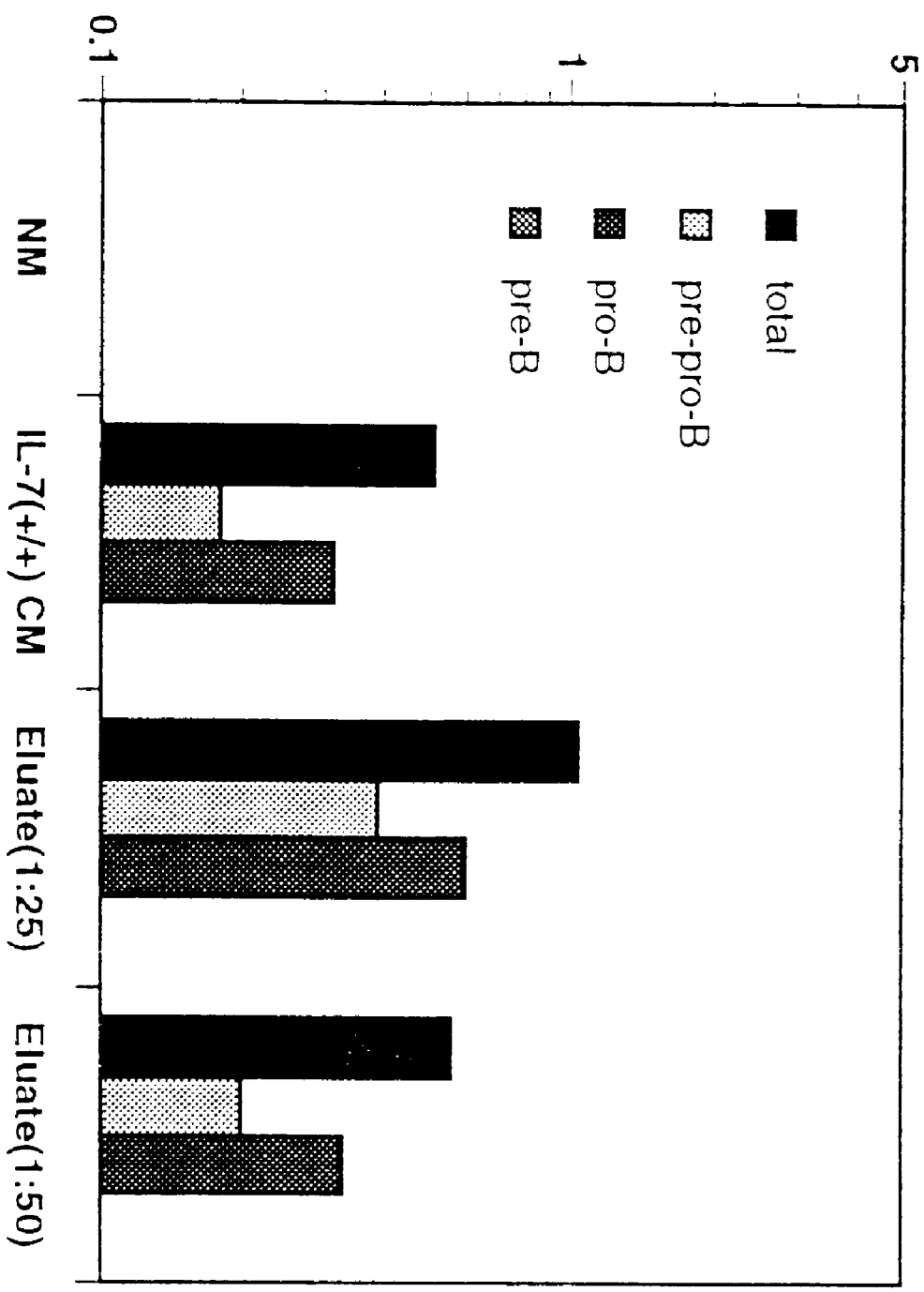
FIG. 6 is a bar graph of the number of cells (total, pre-pro-B, pro-B, and pre-B) found in a IL-7 (+/+) conditioned medium (CM) versus eluate.

Inasmuch as IL-7 is one of the cytokines most closely associated with early B-lineage development, BM adherent cells and stromal cell lines from wild-type and IL-7 gene-deleted (–/–) mice were utilized to investigate its possible regulatory role in the pro-B culture system. The results show that both rIL-7 and IL-7(–/–) CM maintain the viability of pre-pro-B cells from freshly harvested rat BM, but that neither induces them to proliferate and/or differentiate, even in the presence of IL-3, rSCF and/or rIGF. However, as seen in FIG. 5A (primary culture) when added to IL-7(–/–) CM, rIL-7 efficiently stimulates proliferation and differentiation of freshly harvested pre-pro-B cells. Conversely, anti-IL-7 mAb inhibits the expansion of pre-pro-B cells in culture, and adsorbs the pre-pro-B cell growth-stimulating activity from both IL-7(+/+) CM and rIL-7-supplemented IL-7(–/–) CM. Yet, anti-IL-7 mAb does not neutralize the pre-pro-B cell growth-stimulating activity of these CM; and rIL-7 does not restore this activity to anti-IL-7 mAb-adsorbed CM. These results suggest that the pre-pro-B cell growth-stimulating activity in the pro-B culture system is the property of a self-aggregating molecular complex of IL-7 and a second BM stromal cell-derived co-factor (See FIG. 6). The results also suggest that this pre-pro-B cell growth-stimulating factor (PPBSF) not only selectively stimulates proliferation of pre-pro-B cells, but "primes" them and/or their immediate descendants to respond directly to monomeric IL-7 (FIG. 5B, secondary culture).

Figure 7:
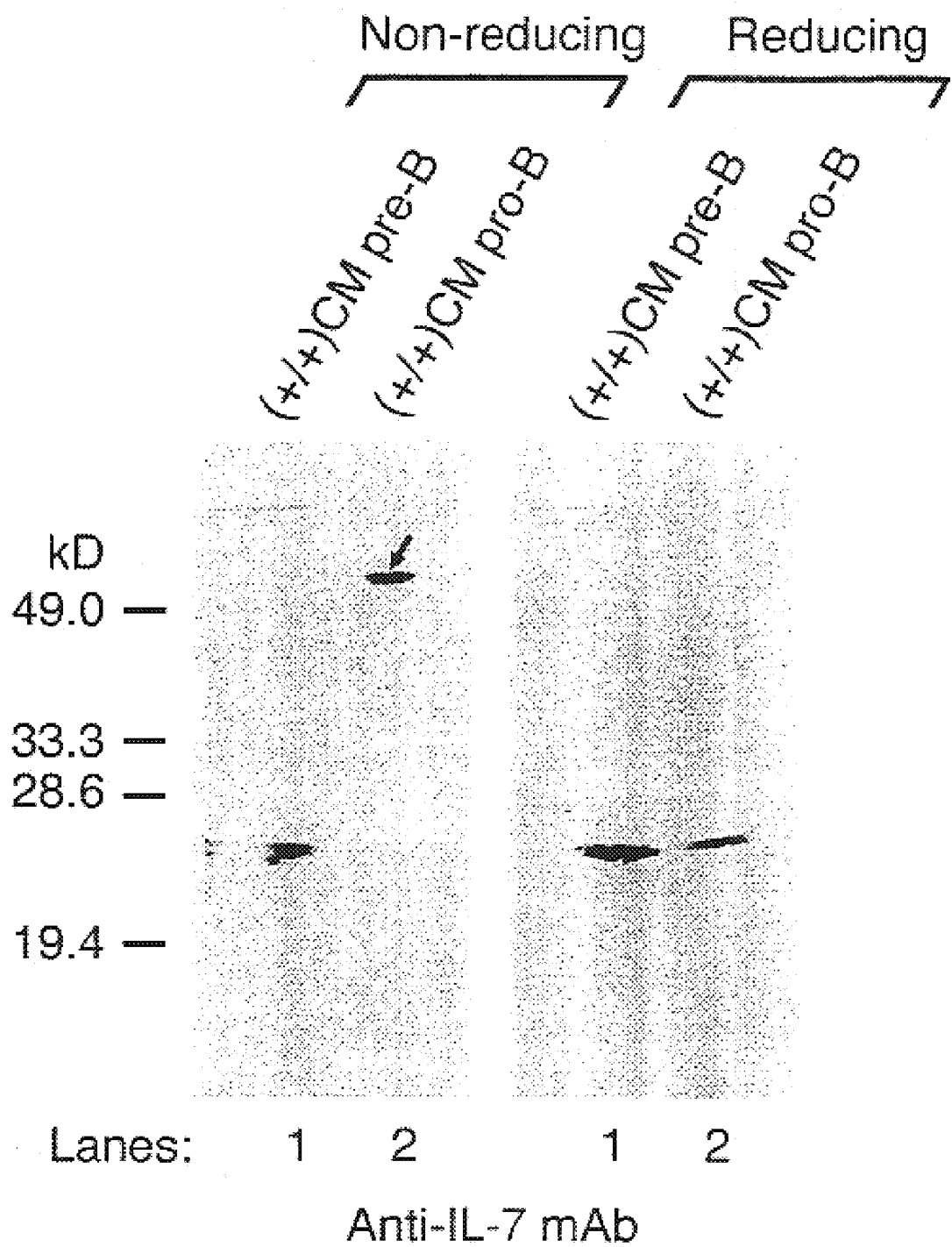
FIG. 7 is a western immunoblot of PPBSF developed with anti-IL-7 monoclonal antibody in pre-B and pro-B cell conditioned medium under reducing and non-reducing conditions.
Figure 8:
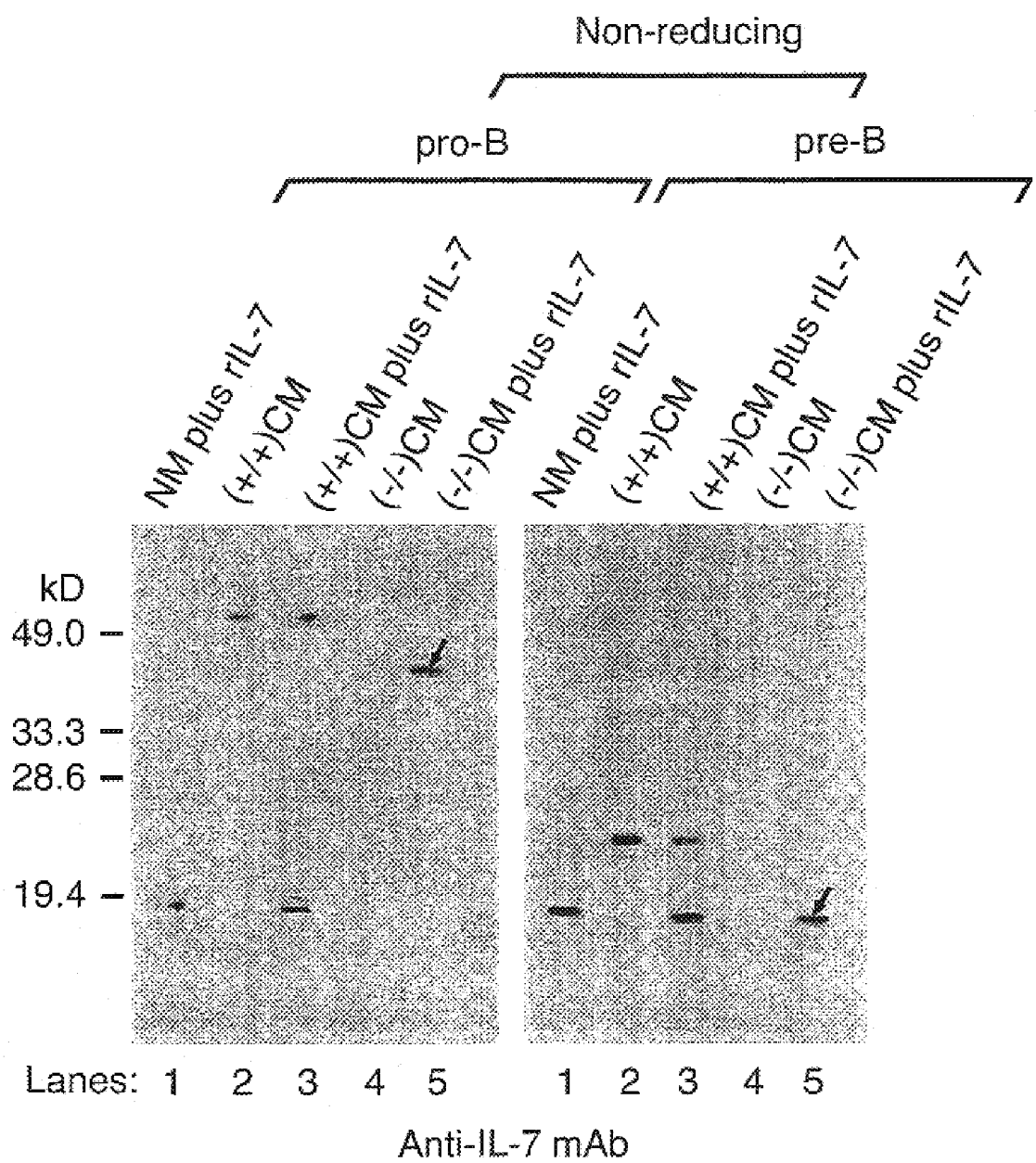
FIG. 8 is a western immunoblot of PPBSF developed with anti-IL-7 monoclonal antibody in designated cell medium with and without rIL-7.
Figure 9:
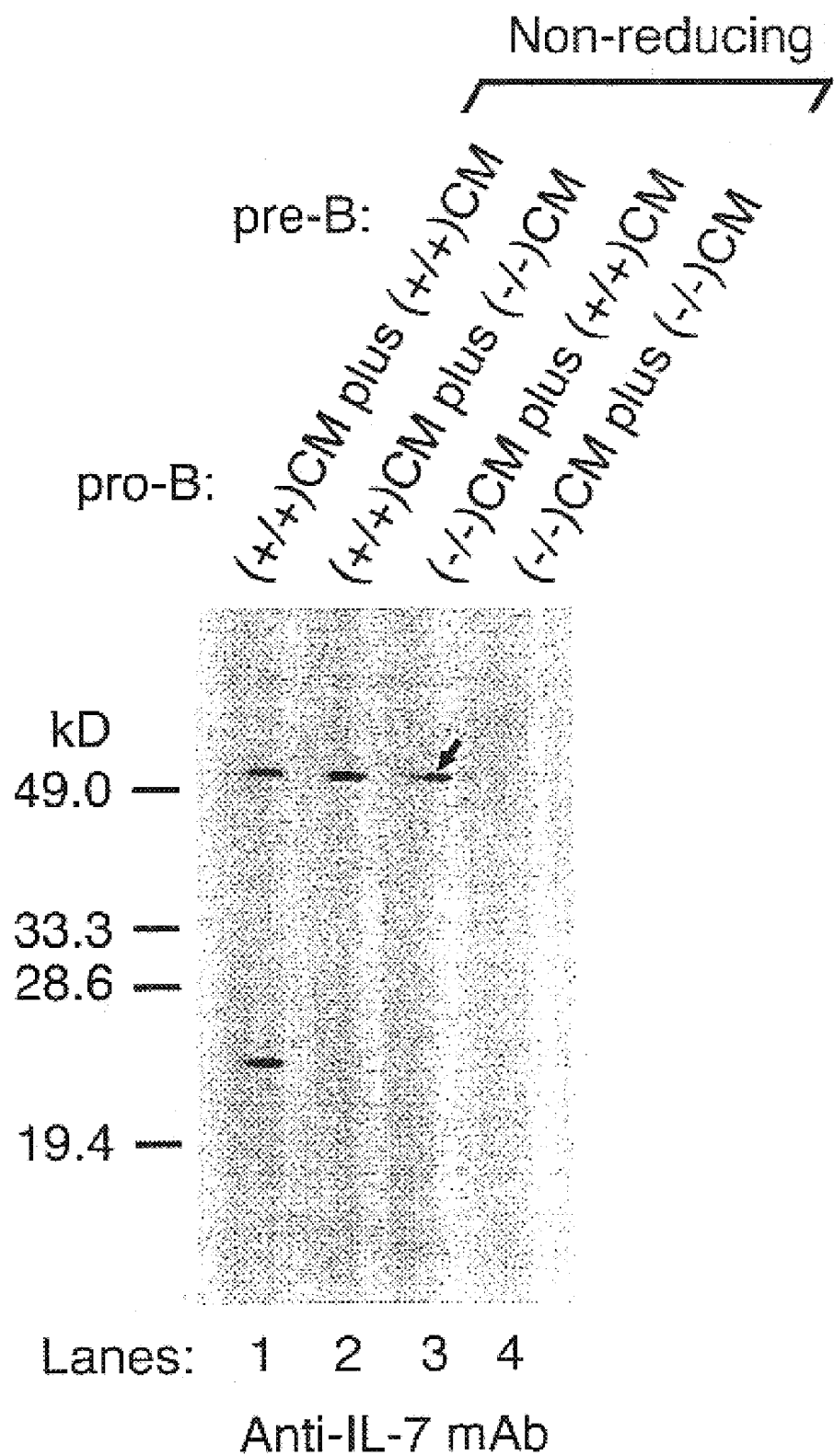
FIG. 9 is a western immunoblot of PPBSF developed with anti-IL-7 monoclonal antibody in designated combinations of conditioned medium.

PPBSF is a Covalently-linked Heterodimer of IL-7 and an Mr. 30,000 Co-factor Direct evidence for the existence of PPBSF in CM generated under pro-B cell, but not pre-B cell, culture conditions is provided by Western immunoblot analysis (FIG. 7). The results demonstrate that, when developed with anti-IL-7 mAb, PPBSF migrates electrophoretically as an apparent 55 kD molecule under non-reducing conditions, whereas the IL-7 component migrates as an apparent 25 kD molecule under reducing conditions. Furthermore, IL-7 exists almost entirely as an heterodimer (i.e. PPBSF) in pro-B-type cultures, and as a monomer in pre-B-type cultures. However, addition of rIL-7 or native IL-7 (from pre-B CM) to CM from IL-7 KO mice results in the rapid formation of apparent 45 kD (FIG. 8, lane 5) and 55 kD (FIG. 9, lane 3) molecular complexes, respectively, both of which have the functional properties of PPBSF.

Figure 10:
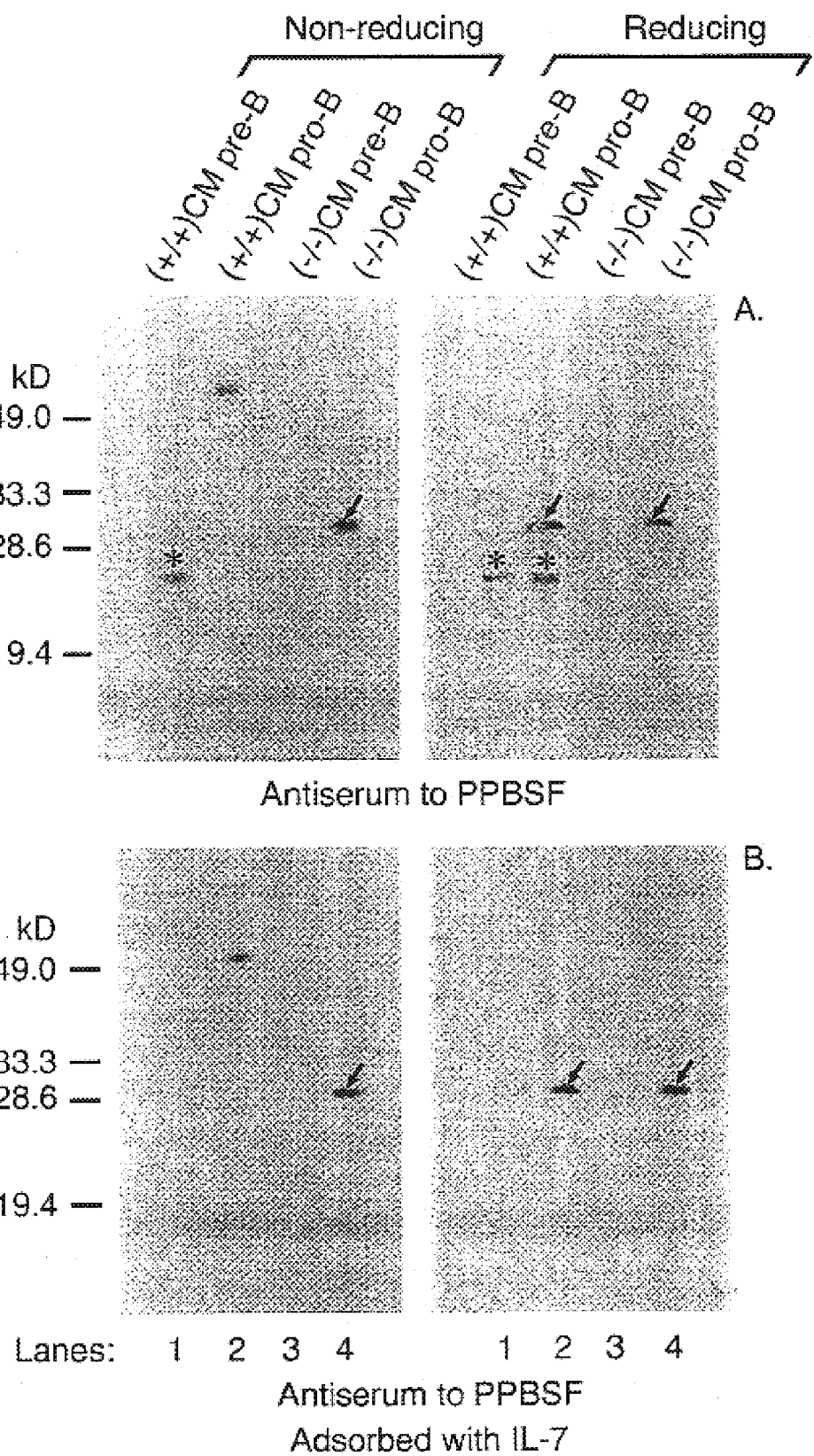
FIG. 10 is a western immunoblot of PPBSF developed with antiserum to PPBSF and adsorbed with IL-7 for designated conditioned medium, under reducing and non-reducing conditions.
Figure 11:
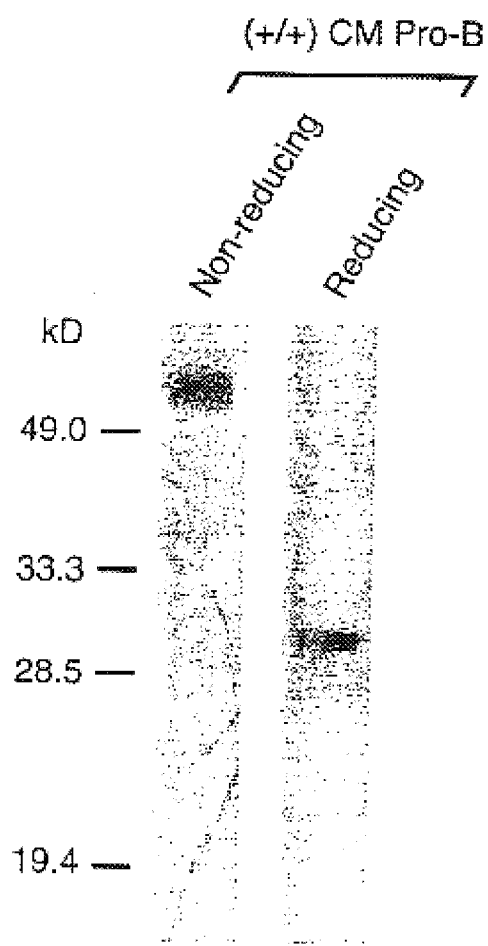
FIG. 11 is a western immunoblot electrophoresed under reducing and non-reducing conditions demonstrating a 30 kD molecule as the non-IL-7 component of PPBSF in (+/+) CM Pro-B.
Figure 12:
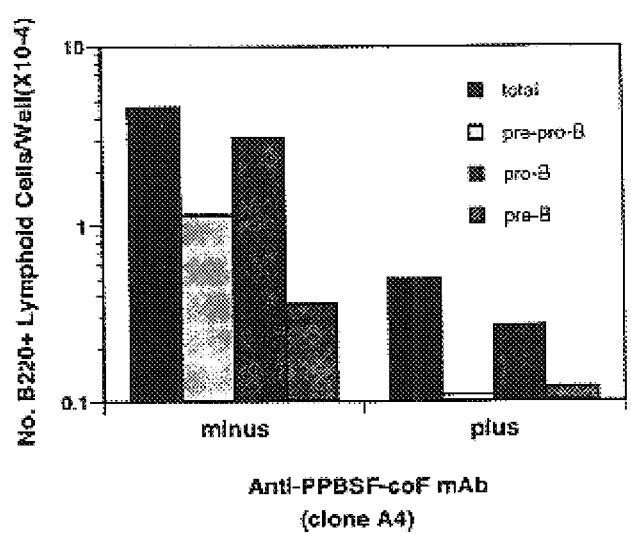
FIG. 12 is a bar graph of the number of B220+ lymphoid cells (total, pre-pro-B, pre-B, pro-B) plus and minus anti-PPBSF-coF monoclonal antibody.

Using a neutralizing antiserum prepared in IL-7(−/−) mice against IL-7(+/+) CM (and subsequently monoclonal antibody (IgG2a; clone A4) against affinity-purified PPBSF), the non-IL-7 component of PPBSF was identified by Western analysis as an apparent 30 kD molecule (FIG. 10, lanes 2 and 4; and FIG. 11). These Abs react with PPBSF-coF in both its heterodimeric and monomeric forms, and neutralize the PPBSF activity in CM (FIG. 12). PPBSF-coF is able to maintain the viability of pre-pro-B cells, but does not stimulate their proliferation unless complexed with IL-7. It is constitutively produced by lines of IL-7(−/−) BM stromal cells under pro-B, but not pre-B-type culture conditions. It does not appear to be SCF, IGF-1, TSLP, Fet3, SDF-I or the soluble form of the IL-7R.

EXAMPLE 6

Determination that PPBSF is a Hybrid Cytokine of IL-7 and the β-chain of Hepatocyte Growth Factor/Scatter Factor (HGF/SF)

Identity of PPBSF-coF

To identify the PPBSF-coF, affinity purified native PPBSF was electrophoresed under reducing conditions and the 30 kDa band was subjected to amino acid analysis. The results demonstrated that the first 15 of 17 amino acid residues were identical to the published sequence of mouse HGF β-chain (FIG. 13), as was the overall molecular mass of the peptide. The identity of PPBSF-coF as the HFG β-chain was confirmed by reciprocal Western blot analyses, in which antibodies to HGF β-chain reacted with purified native PPBSF-coF, and mAbs to PPBSF-coF reacted with rHGF. In addition, both anti-HGF and anti-HGFβ antibodies neutralized the PPBSF activity in IL-7 (+/+) CM.

Identification and Cloning of a Variant of HGF mRNA

Figure 16:
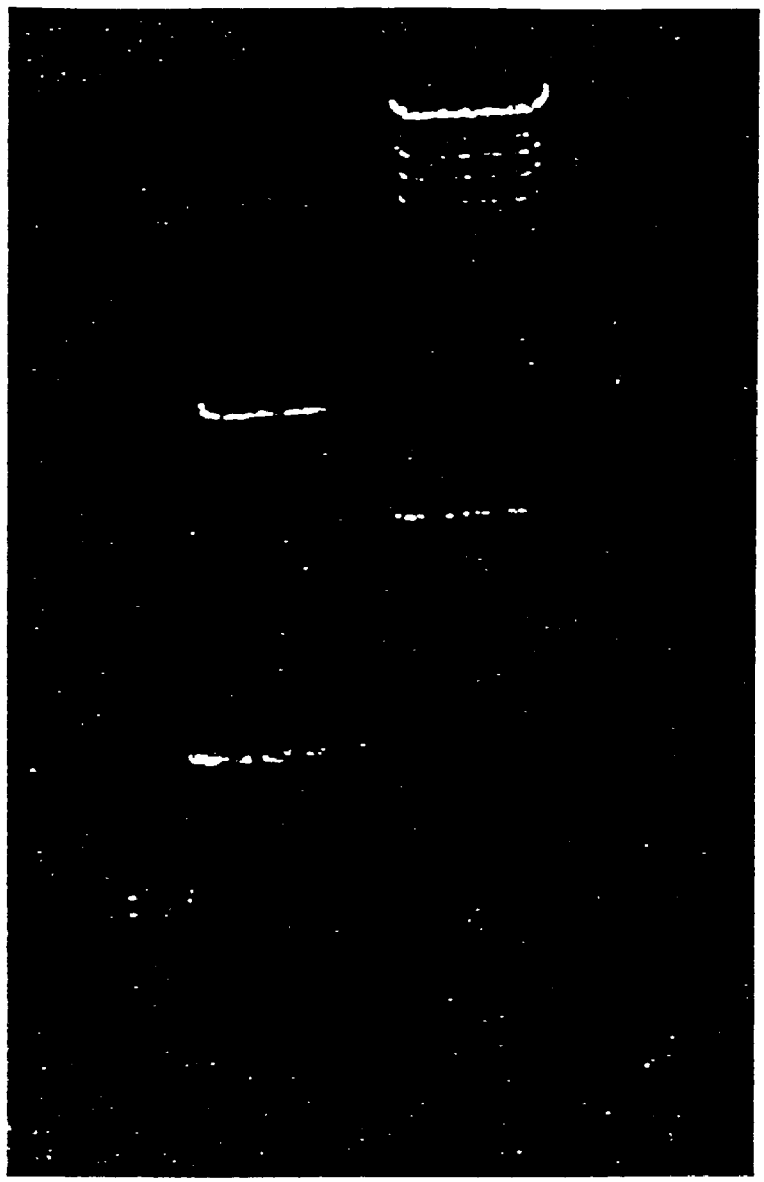
FIG. 16 is gel electrophoresis illustrating RT-PCT analysis of the HFG mRNA transcripts from mouse BM stromal cells. First-stand cDNA from cultured IL-7 (−/−) mouse BM stromal cells subjected to PCR with primers designed to amplify the entire coding sequence of mouse HGF. The blot demonstrates both the 2230 bp product corresponding to the full-length HGF and a novel 840-bp product, corresponding to HGFβ chain.

Total RNA was isolated with TRI$_{zotm}$ Reagent (Total RNA Isolation Reagent, Life Technologies, Gaithersburg, Md.) from IL-7 (−/−) BM stomal cells. Random-primed first-strand cDNA was generated from this RNA using MMLV reverse transcriptase (RETRO Script™, Amibion, Austin, Tex.). PCR reactions were performed with the cDNA, Taq polymerase (Life Technologies, Gaithersburg, Md.), and primers designed to amplify the entire coding sequence of mouse HGF: 5'-CAGTCTGCTCGAACTGCA-3' (in 5'flanking region) 5'-TGGCCTCTTCTATGGCTA-3' (in 3' flanking region). Two RT-PCR products were obtained when the amplified fragments were separated on 1% agarose gel and visualized by ethidium bromide (FIG. 16). One of these products corresponded to the full-length HGF cDNA (2230 bp). However, the second product was 840 bp long, the same as the coding sequence of HGFβ. The cDNA of the shorter PT-PCR product was cloned, and the nucleotide sequence was found to concur precisely with the published mouse HGFβ cDNA sequence. Furthermore, although the HGFα chain cDNA was completely absent, the signal sequence was identical to that in full-length HGF cDNA.

EXAMPLE 7

Formation and Biological Activity of Heterodimes of rIL-7 and rHGFβ

Production of Recombinant HGFβ Proteins

Figure 14:
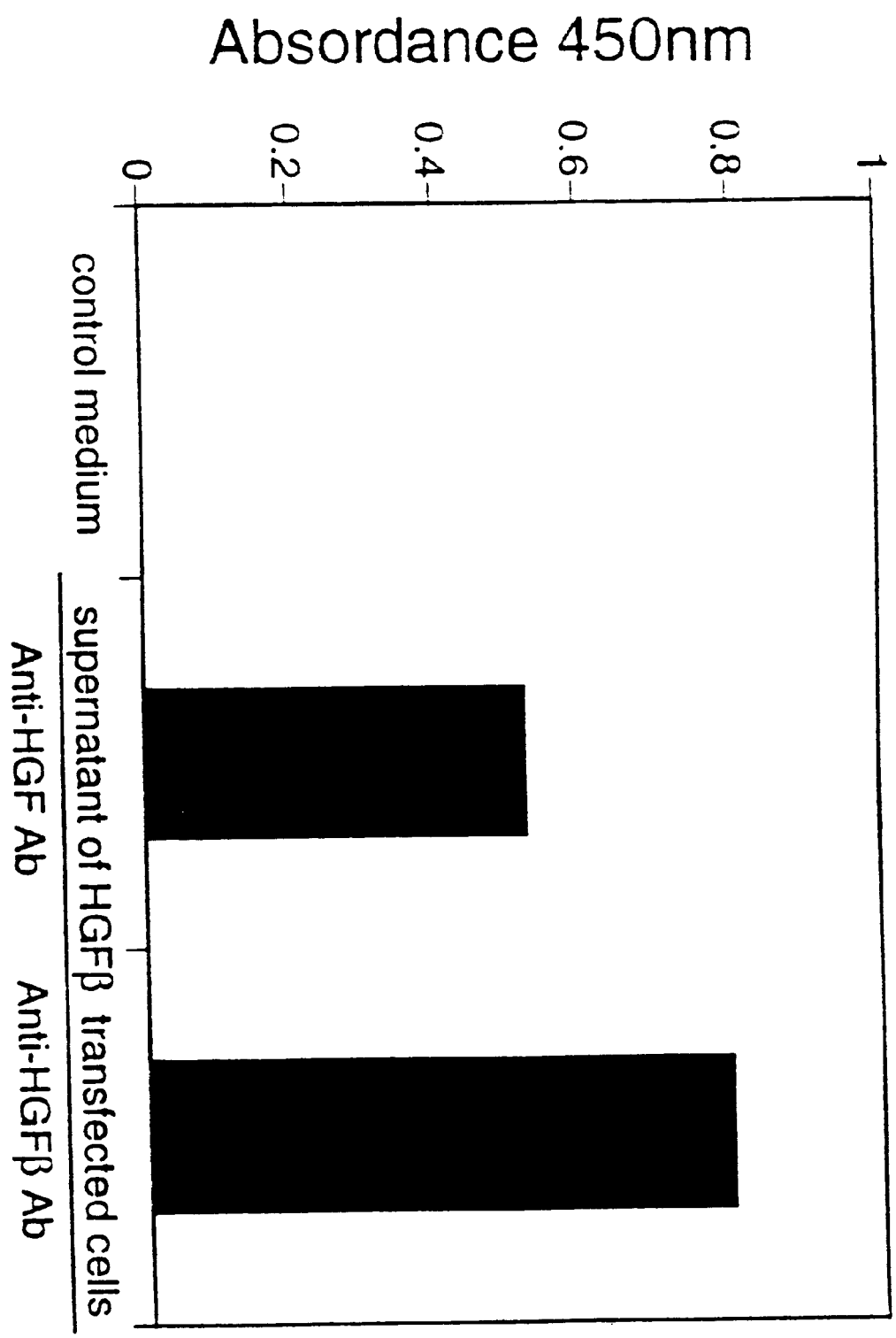
FIG. 14 is a bar graph of HGFβ expression in CHO cells transfected with a mammalian expression vector into which the HGFβ was cloned versus control medium.

The PCR-amplified splice variant was subcloned into the mammalian expression vector pcDNA3.1 (+) (Invitrogen). The plasmid was transfected into Chinese hamster ovary (CHO) cells (LIPOFECTAMINE Plus™ Reagent, Life Technologies). The serum-free supernatant from the transfected CHO cells was collected, concentrated 10× and filtered to remove any cells and evaluated for the production of HGFβ protein by ELISA using anti-HGF β antibodies. The supernatant of transfected cells with vector but without HGFβ gene was used as control medium. HGFβ protein was detected in the supernatant of HGFβ-transfected cells, but not in that of the empty vector-transfected cells (FIG. 14). The HGFβ gene was also subcloned into prokaryotic fusion protein expression vector pCAL-n (Stratagene, La Jolla, Calif.) and transformed into E.coli BL21(DE3). The fusion protein was purified by calmodulin affinity, and rHGFβ, released by thrombin, was detected as a single band by SDS-PAGE and Western blotting.

EXAMPLE 8

Figure 17:
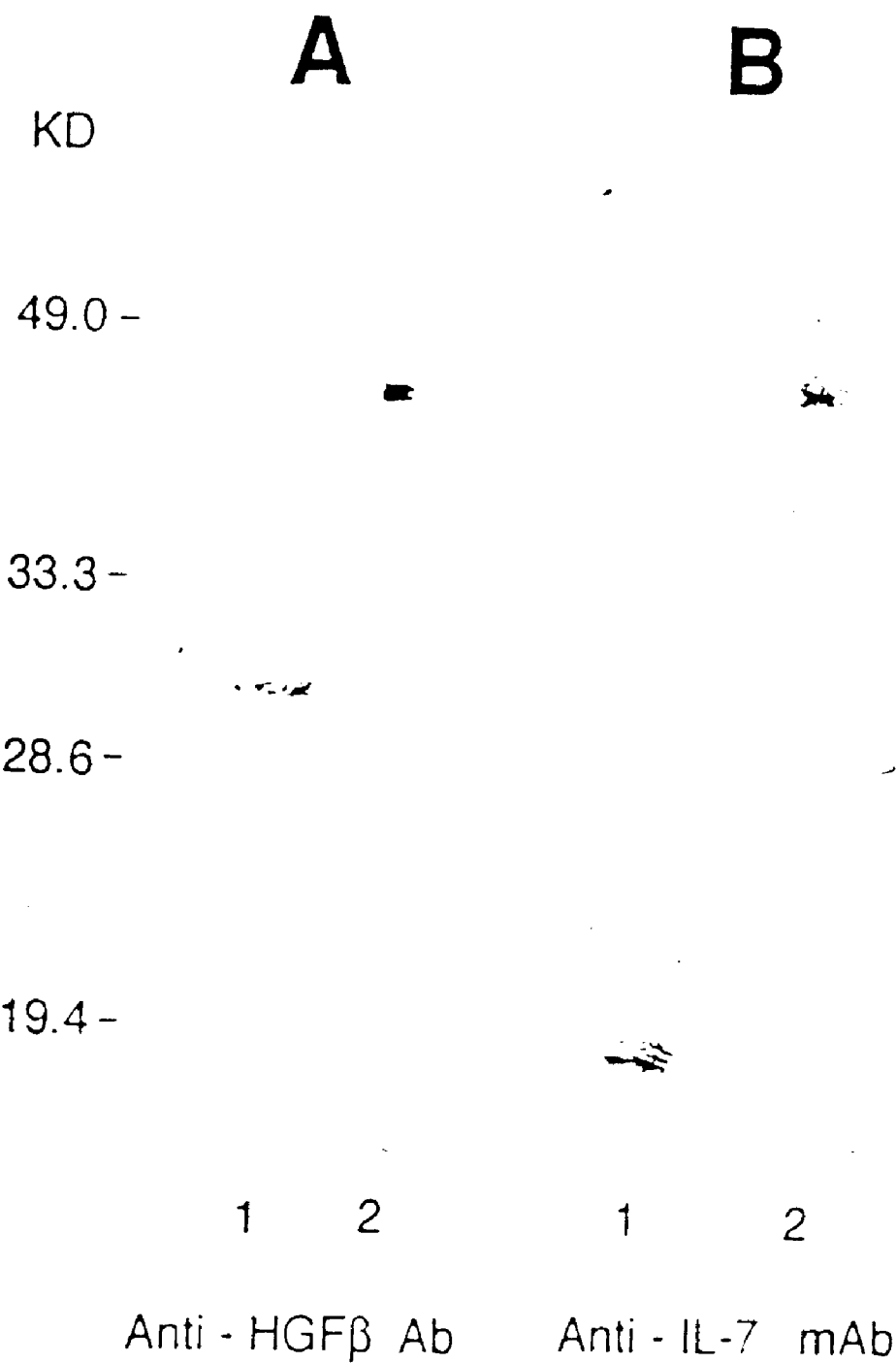
FIG. 17 is a western blot illustrating that recombinant IL-7 forms a heterodimer with rHGFβ in the presence of low molecular weight heparan-sulfate derived oligosaccharides. Equimolar concentrations of rIL-7 and rHGFβ were mixed in the presence and absence of low molecular weight heparan sulfate-derived oligosaccharides. One hour later the mixtures were electrophoresed and developed with (A) anti-HFGβ Ab or (B) anti-IL-7 mAb. In each instance as shown, a 45 kD heterodimer was observed in the presence (lane 2), but on the absence (lane 1) of, heparan sulfate.

Formation of a Biological Activive of Heterodimer of rIL-7 and rHGFβ Using Low Molecular Weight Heparin Sulfate Oligosaccharides As both IL-7 and HGF are heparin-binding molecules, the present inventors tested the ability of rIL-7 and rHGFβ to from a heterodimer when equimolar ratios were mixed in serum-free medium in the presence or absence of low molecular weight heparin sulfate (HS)-derived oligosaccharides. The reactants were electrophoresed under nonreducing conditions and subjected to Western blot analysis. The results in FIG. 17 show that rHGFβ migrated at 30 kD when added to rIL-7 in the absence of the HS-derived oligosaccharides, and at 45 kD in their presence. Similarly, rIL-7 migrated at 14.5 kD when added to rHGFβ in absence of HS-derived oligosaccharides, and at 45 kD in their presence. Hence, rIL-7 and HGFβ form an heterodimer in the presence of low molecular weight HS-derived oligosaccharides. Comparable results were obtained when FBS, rather than HS-derived oligosaccharides, was added to the medium.

Figure 15:
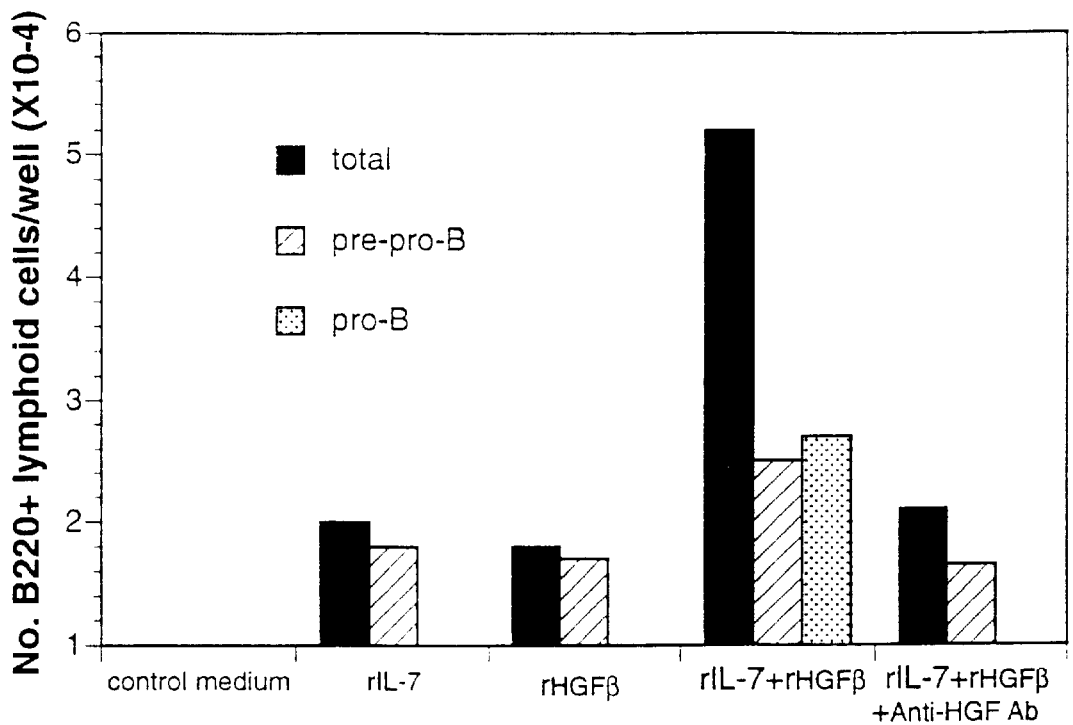
FIG. 15 is a bar graph of pre-pro-B cell growth stimulating activity of the combination of rIL-7 and rHGFβ.

To determine if the IL-7/HGFβ heterodimer had biological activity, freshly harvested rat BM cells were incubated in culture medium containing 20% FBS plus rIL-7 and/or 2×supernatant of HGFβ transfected cells in the absence of anti-HGFβ Ab. Lymphoid cells were harvested and phenotyped on day 10. Both rIL-7 and the supernatant of HGFβ- gene transfected cells (or purified rHGFβ therefrom) were able to maintain the viability of pre-pro-B cells, but neither was able to stimulate their proliferation or to induce their differentiation to pro-B cells. However, when added concurrently, these reagents stimulated a significant increase in the generation of both pre-pro-B cells and pro-B cells (FIG. 15). Furthermore, this activity could be neutralized by anti-HGFβ antibody. Similar results were obtained when the purified heterodimer of rIL-7 and rHGFβ performed in the presence of HS-derived oligosaccharides, was used.

EXAMPLE 9

Analysis of B-Cell Development in Interleukin (IL)-7 Gene-deleted Mice

Maturation Arrest Occurs at the Late Pro-B cell Stage (Fr.C')

Figure 18:
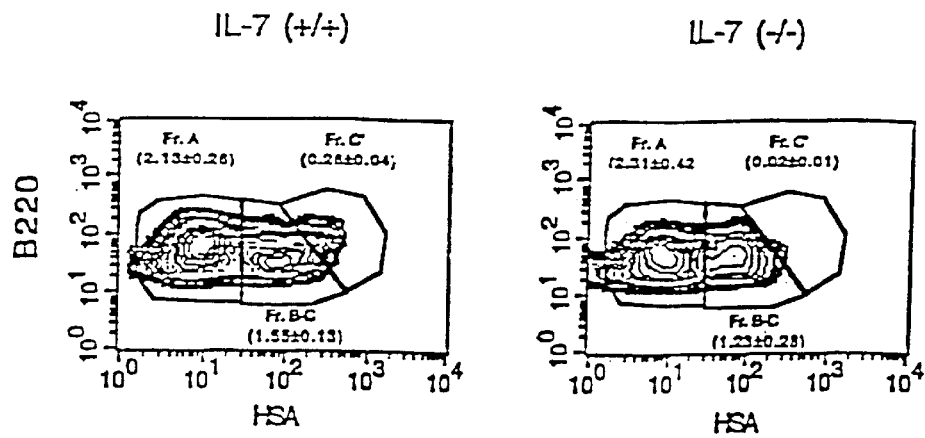
FIGS. 18–21 are flow cytometry histograms of B-cell populations (pre-pro-B, (Fr.A), pro-B (Fr.B-C), and pre-B (Fr.C')) (FIG. 18) in IL-7 knock-out mice with population fractions demonstrating expression of IL-7Rα (FIG. 19), TdT (FIG. 20), and Cμ (FIG. 21)
Figure 19:
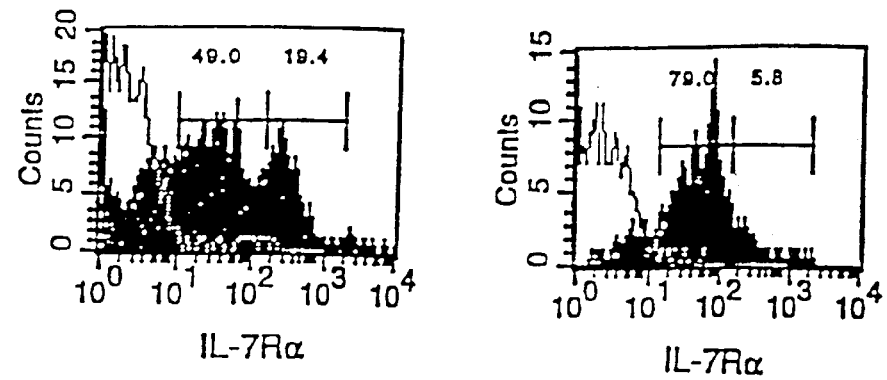
Figure 20:
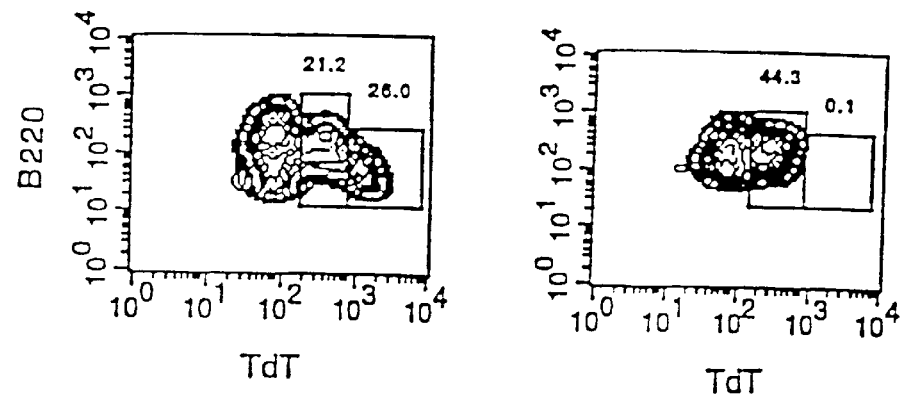
Figure 21:
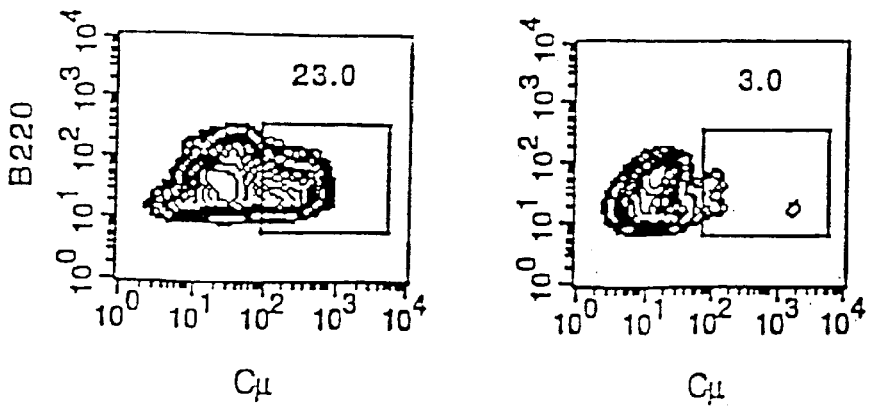

Bone marrow cells from IL-7 KO mice were stained for the expression of B220, CD43, HSA and/or BP-1, as analyzed by FCM according to the scheme of Hardy et al., J. Exp. Med. 173: 1213–1225 (1991). The data in FIG. 18 indicate that: (a) the number of Fr A (pre-pro-B) cells is normal; (b) Fr B and C (pro-B) cells are slightly reduced; and (c) Fr C', which is the transitional stage from pro-B to pre-B cells is missing. Furthermore, the expression of CD25, which has been suggested to distinguish cells undergoing VDJ from those undergoing DJ gene rearrangement was severely reduced. In addition, up-regulation of IL-7Rα and TdT, normally observed during pre-pro-B to pro-B cell differentiation, did not occur (FIGS. 19 and 20); neither did cμ expression of the late pro-B cell (transitional) stage (FIG. 21). Hence, although IL-7 is not essential for the development of pro-B cells in BM, it is necessary for several key aspects of their differentiation.

Similar Defects Occur in γc KO and Jak3 KO Mice

Like their counterparts in IL-7 KO mice, pro-B cells from γc KO and Jak3 KO mice arrest at Fr C' and express abnormally low levels of TdT, IL-7Rα and cμ. Conversely, despite also arresting at Fr C', pro-B cells from λ5 KO mice and RAG-1 KO mice upregulate TdT and IL-7Rα, and the former express normal levels of cμ. Taken together, these results suggest that signaling through the IL-7Rα/γc/Jak3 complex is essential for upregulation of TdT and IL-7Rα, for expression of cμ, and for the efficient development of cells beyond the pro-B cell stage.

EXAMPLE 10

Effect of PPBSF and rIL-7 in IL-7 KO Mice

Because rIL-7 supported the proliferation and differentiation of pro-B cells from IL-7 KO mice in the presence of IL-7 −/− BM stromal cells, and IL-7-depleted CM from IL-7 +/+ stromal cells was not functionally reconstituted by rIL-7, it was suspected that PPBSF, the heterodimeric form of IL-7, was the responsible factor in the pro-B culture system. This was confirmed by demonstrating that pretreatment with purified PPBSF enabled pro-B cells from IL-7 KO mice to respond to rIL-7. The in vivo administration of rIL-7 to IL-7 KO mice may correct the abnormalities in pro-B cell development by forming PPBSF in BM with the stromal cell derived PPBSF cofactor. It may be postulated that the in vivo administration of anti-IL-7 mAb prevents the production or survival of pro-B cells in IL-7 competent mice by simultaneously eliminating monomeric IL-7 and PPBSF. However, some level of redundancy by other cytokines, such as IL-3 and TSLP, may partially compensate for the role of PPBSF. The fact that both components of the PPBSF heterodimer are avidly bound by heparin sulfate oligosaccharides, as disclosed, may suggest that PPBSF may function as a cell surface and/or ECM-bound molecular complex.

A more specific answer to the above question appears to reside in the ability of PPBSF to selectively regulate the proliferation and differentiation of pre-pro-B cells, which normally express low levels of the IL-7Rα; and of monomeric IL-7 to regulate the G1/S transition and differentiation of pro-B cells, which normally express high levels of the IL-7Rα. As PPBSF does not stimulate proliferation of pro-B cells and IL-7 does not stimulate proliferation of pre-pro-B cells, it would appear that PPBSF induces pre-pro-B cells to become IL-7-responsive pro-B cells by up-regulating the expression of IL-7Rα.

PPBSF, But Not rIL-7, Upregulates TdT and IL-7Rα on Pro-B Cells from IL-KO Mice in vitro rIL-7 stimulated marked in vitro proliferation of pro-B cells from IL7 (+/+) and RAG-1 (−/−) mice, but not from IL-7 (−/−) mice. Conversely, native PPBSF (but not rIL-7 or PPBSF-coF alone) not only upregulated the expression of IL-7Rα, TdT, and cμ in pro-B cells from IL-7 (−/−) mice, but "primed" them to proliferate in response to rIL-7. These results strongly support our working hypothesis that, in addition to stimulating the proliferation and differentiation of pre-pro-B cells, PPBSF up-regulates the expression of high affinity IL-7R, thereby enabling pro-B cells to respond to monomeric IL-7. Significantly, PPBSF also "primed" pro-B cells from IL-7 KO mice to proliferate to rIL-3 in the absence of IL-7.

In vivo Treatment with rIL-7 Restores B Cell Development in IL-7 KO Mice

IL-7 KO mice were injected i.p. daily with rIL-7 to confirm the essential role of IL-7 on early B cell development in vivo. As shown in FIG. 22A, the proportion of B220$^+$ CD43$^+$ (Fr. A-C') cells among total BM cells progressively increased during the first 7 days of treatment, and that of B220$^+$ CD43$^-$ (Fr. D-F) cells between days 7 and 12. Subset analysis with HSA (FIG. 22B) and sIgM (FIG. 22C) showed sequentially overlapping increases in pro-B cells (Fr. B-C), transitional cells (Fr. C'), pre-B cells (Fr. D) and immature B cells (Fr. E) between days 4 and 12. However, at day 12, the proportion of mature B cells (Fr. F) did not exceed that at day 0 (i.e. 10% of normal).

Other studies have shown that within 4 days of i.p. administration of rIL-7, the expression of IL-7Rα, TdT and cμ by pro-B cells and transitional pre-B cells was restored to normal levels in BM of IL-7 KO mice; and these cells were responsive to further stimulation with rIL-7 in vitro. Pre-B cell development was detected in vivo by day 7 of rIL-7 treatment, and sIgM$^+$ B-cell development by day nine. It remains to be determined if the effects of IL-7 reconstitution in IL-7 KO mice (especially at the pre-pro-B and pro-B cell stages) is due to the formation of PPBSF in vivo.

In vivo Treatment with rIL-7 Enables B220$^+$ CD43$^+$ B-lineage Cells from IL-7 KO Mice to Respond to rIL-7 in vitro The present inventors have previously demonstrated that pro-B cells in IL-7 KO mice express abnormally low levels of IL-7Rα, TdT and cμ, and that expression of these proteins increases to normal levels after in vivo reconstitution with rIL-7.

Figures 23A, 23B:
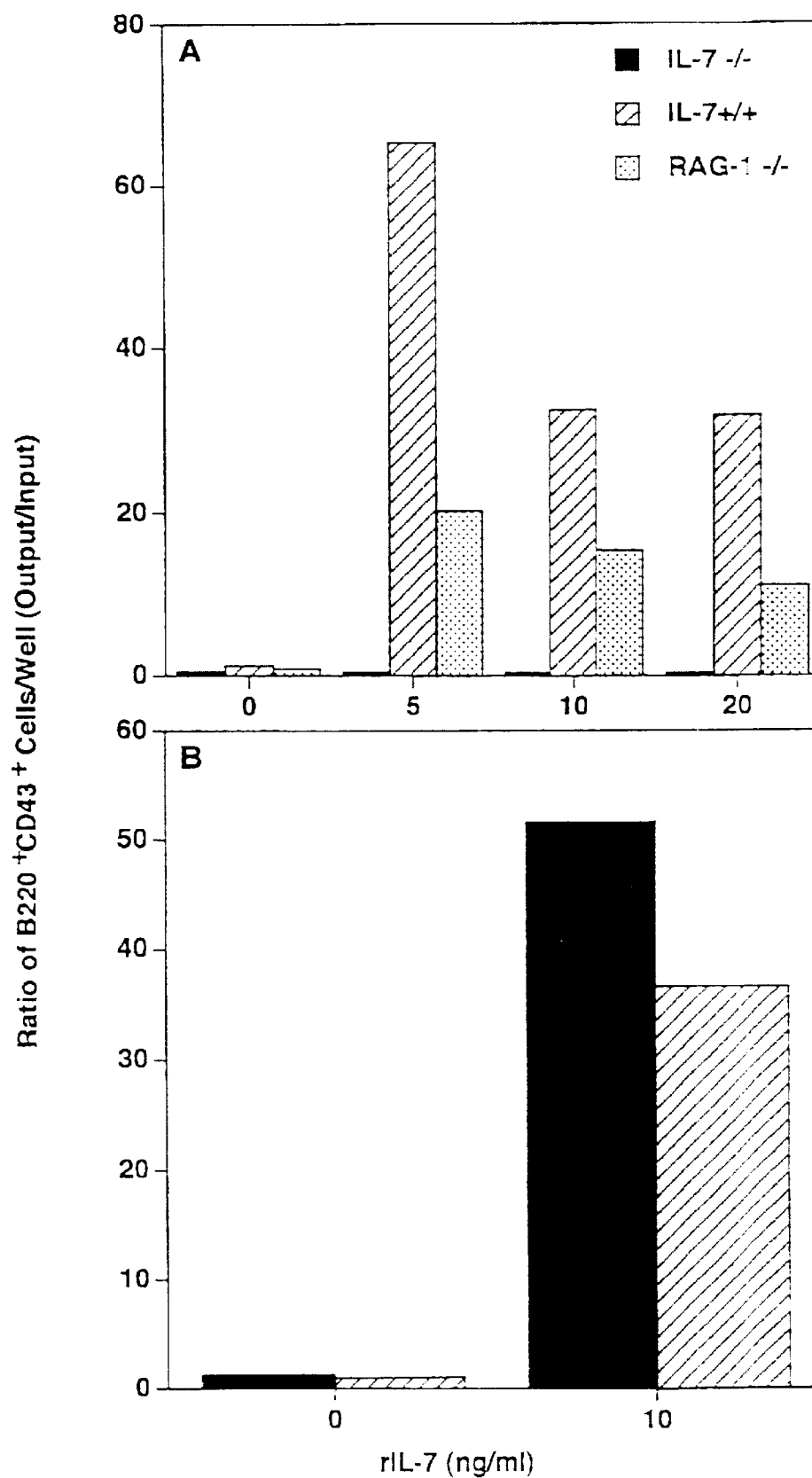
FIGS. 23A and 23B are bar graphs demonstrating the ability of rIL-7 to support the generation of B220$^+$ CD43$^+$ cells from IL-7 KO mice in vitro. 1×10$^6$ BM cells from IL-7 KO (−/−) mice, obtained (A) before or (B) 4 days after the onset of in vivo treatment with rIL-7, were incubated with medium (RPMI 1640 supplemented with 5% FBS and 5×10$^{-5}$ M 2ME) containing the indicated concentrations of rIL-7. BM cells from untreated IL-7 competent (+/+) and RAG-1 KO (−/−) mice were incubated under the same culture conditions. Cells were harvested 4 days later and the results were expressed as the ratio of the input and output numbers of B220$^+$ CD43$^+$ cells/well.

As illustrated in FIG. 23A that BM cells from IL-7 KO mice, unlike those from WT and RAG-1 KO mice, fail to generate B220$^+$ CD43$^+$ pre-pro-B/pro-B cells in vitro when stimulated with graded concentrations of rIL-7. In contrast, BM cells from day 4 rIL-7-reconstituted IL-7 KO mice were as efficient as were those from IL-7 competent mice in generating B220$^+$ CD43$^+$ cells when stimulated in vitro with rIL-7 (FIG. 23B). The RAG-1 KO mice, whose pro-B cells express normal levels of IL-7Rα and TdT, were included to control for the absence of cμ expression, pre-BCR formation and Fr C' cells in IL-7 KO mice. Although these defects substantially reduced the maximal level of responsiveness to rIL-7 (FIG. 23A), a 20-fold increase in the number of B220$^+$ CD43$^+$ cell/well above input levels was still observed.

Figure 24:
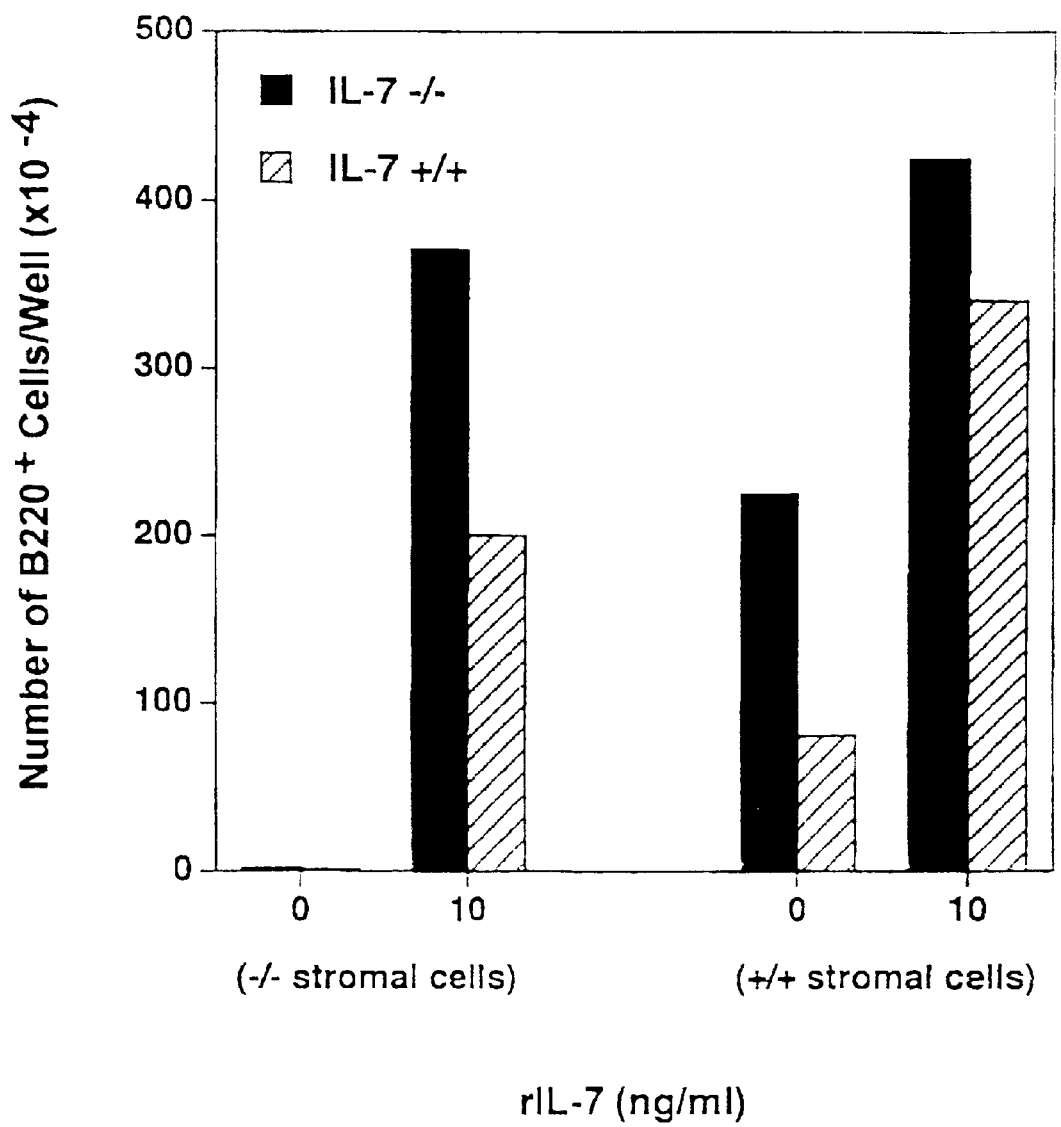
FIG. 24 is a bar graph demonstrating the ability of BM stromal cells from IL-7 +/+ or IL-7 −/− mice to support the in vitro generation of B-lineage cells from IL-7 KO mice in the presence or absence of rIL-7. 1×10$^6$ BM cells from IL-7 +/+ and IL-7 −/− mice were incubated in the presence or absence of 10 ng/ml rIL-7 on stromal cell layers established from either IL-7 +/+ or IL-7 −/− mice. Cells were harvested on day 10 and the number of B220$^+$ cells per well were calculated.

Both rIL-7 and BM Stromal Cell-derived Signals are Required to Stimulate B220$^+$ CD43$^+$ Cells from IL-7 KO Mice in vitro Since rIL-7 was not sufficient to stimulate B220$^+$ CD43$^+$ BM cells from untreated IL-7 KO mice to proliferate in vitro, it was determined whether BM stromal cell layers could provide the necessary additional signals. As shown in FIG. 24, IL-7 −/− as well as IL-7 +/+ BM stromal cell layers enabled rIL-7 to support the growth of B-lineage cells in vitro. Although, IL-7 +/+ BM stromal cells were sufficient by themselves, additional growth occurred in the presence of rIL-7.

Figure 25A:
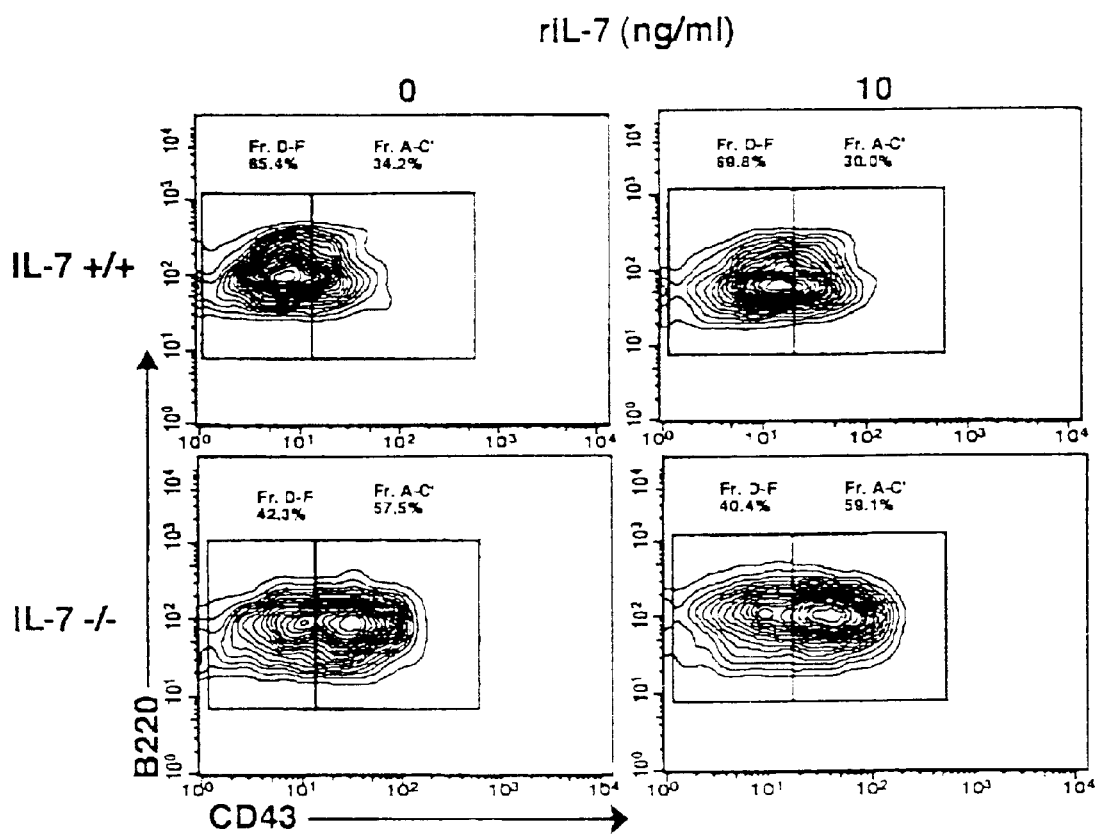
FIGS. 25A and 25B are flow cytometry histograms demonstrating phenotypic analysis of B-lineage cells generated in vitro on IL-7 +/+ BM stromal cells in the presence or absence of rIL-7. Day 10 culture-generated B-lineage cells from IL-7 +/+ and IL-7 −/− mice (see FIG. 23, +/+ stromal cells) were analyzed for the expression of B220, CD43 and IL-7Rα. (A) Proportions of CD43$^+$ (Fr. A-C') and CD43$^-$ (Fr. D-F) cells among the B220$^+$ population. (B) Proportions of IL-7Rα$^{lo}$ and IL-7Rα$^{hi}$ cells among the B220$^+$ CD43$^+$ population. Fewer than 10% Fr. D-F and 5% IL-7Rα$^{hi}$ cells were present in the input population (day 0)
Figure 25B:
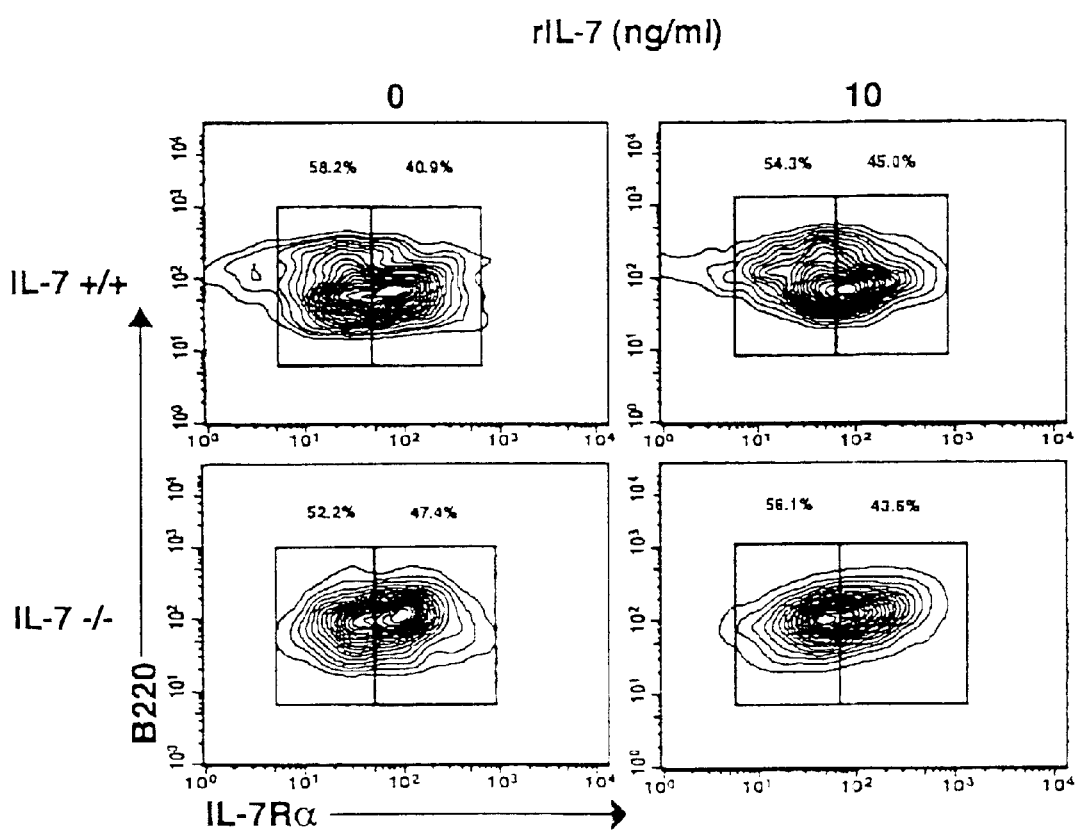
Figure 26:
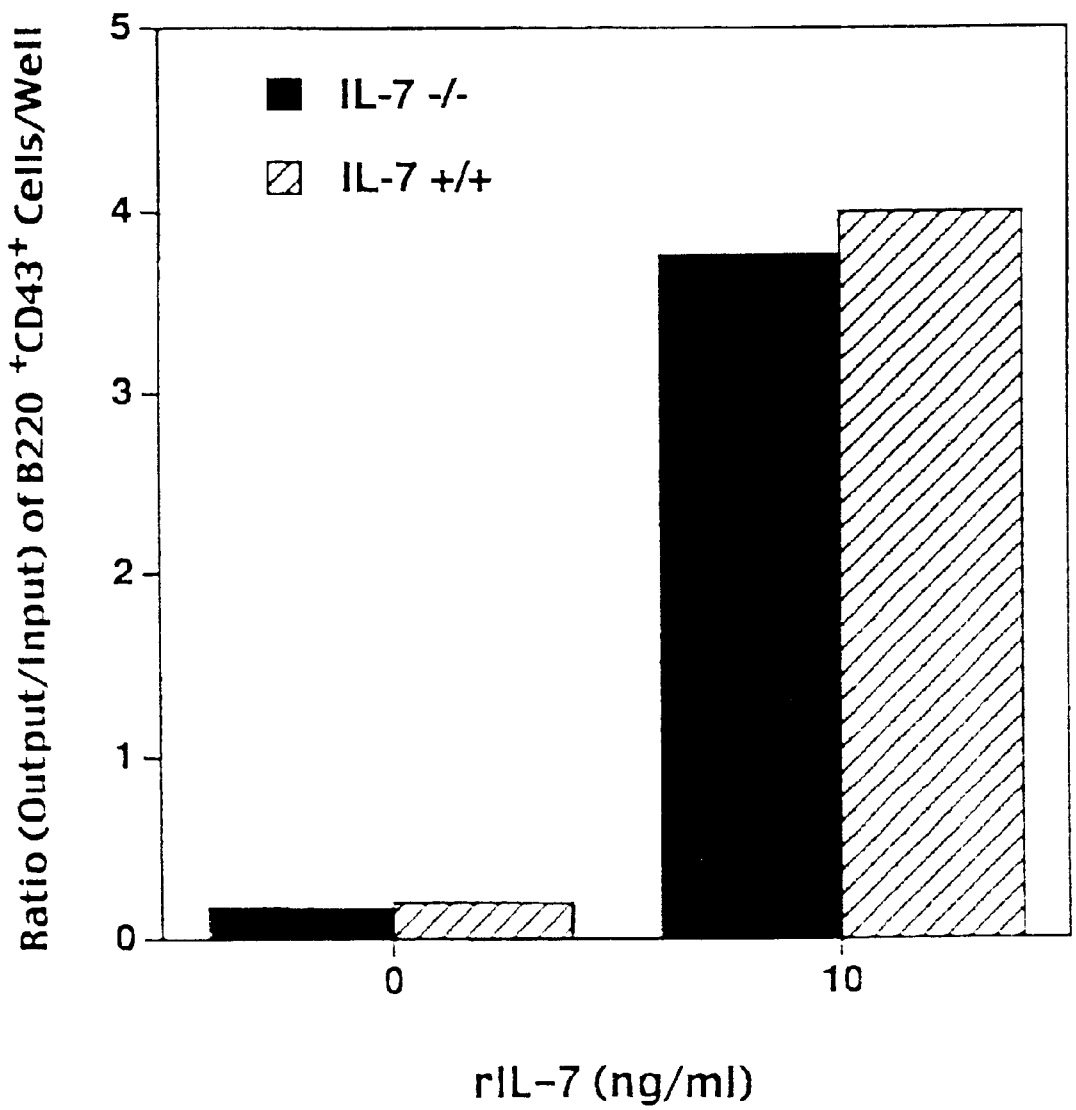
FIG. 26 is a bar graph demonstrating the ability of culture-generated B-lineage cells from IL-7 KO mice to respond to rIL-7 alone. 1×10$^5$ B-lineage cells from day 10 primary cultures containing +/+ stromal cells and 10 ng/ml rIL-7 (see FIG. 23) were transferred into secondary cultures containing medium only or medium plus 10 ng/ml rIL-7. Cells were harvested 4 days later and the numbers of B220$^+$ CD42$^+$ cells/well were determined. Results are expressed as the ratio of output to input numbers of cells/well.

Phenotypic analysis of the IL-7 KO B-lineage cells generated in primary cultures containing IL-7-competent stromal cells showed that approximately 40% had matured to at least the pre-B cell stage (B220$^+$ CD43$^-$) and that additional rIL-7 was not required, (FIG. 25A). Examination of the pre-pro-B/pro-B (B220$^+$ CD43$^+$) cell fraction from these cultures (FIG. 25B) revealed that the expression of IL-7Rα was up-regulated on about 45% of the IL-7 KO cells. Furthermore, when the B220$^+$ cells from these primary cultures were transferred to stromal cell-deficient secondary cultures, they continued to proliferate in response to rIL-7 alone (FIG. 26).

Up-regulation of IL-7Rα Expression on B220$^+$ CD43$^+$ Cells from IL-7 KO Mice in vitro The growth to the pre-pro-B and pro-B cell stages was restricted by using the stromal-cell-dependent pro-B cell culture system, as optimized for mouse BM cells by the presence of both IL-7 +/+ BM stromal cells and 10 μg/ml rIL-7. As in the pre-B-type cultures (FIG. 25B), up-regulated expression of IL-7Rα was observed on approximately 50% of the IL-7 KO B220$^+$ CD43$^+$ cells generated in pro-B-type cultures.

Figure 27:
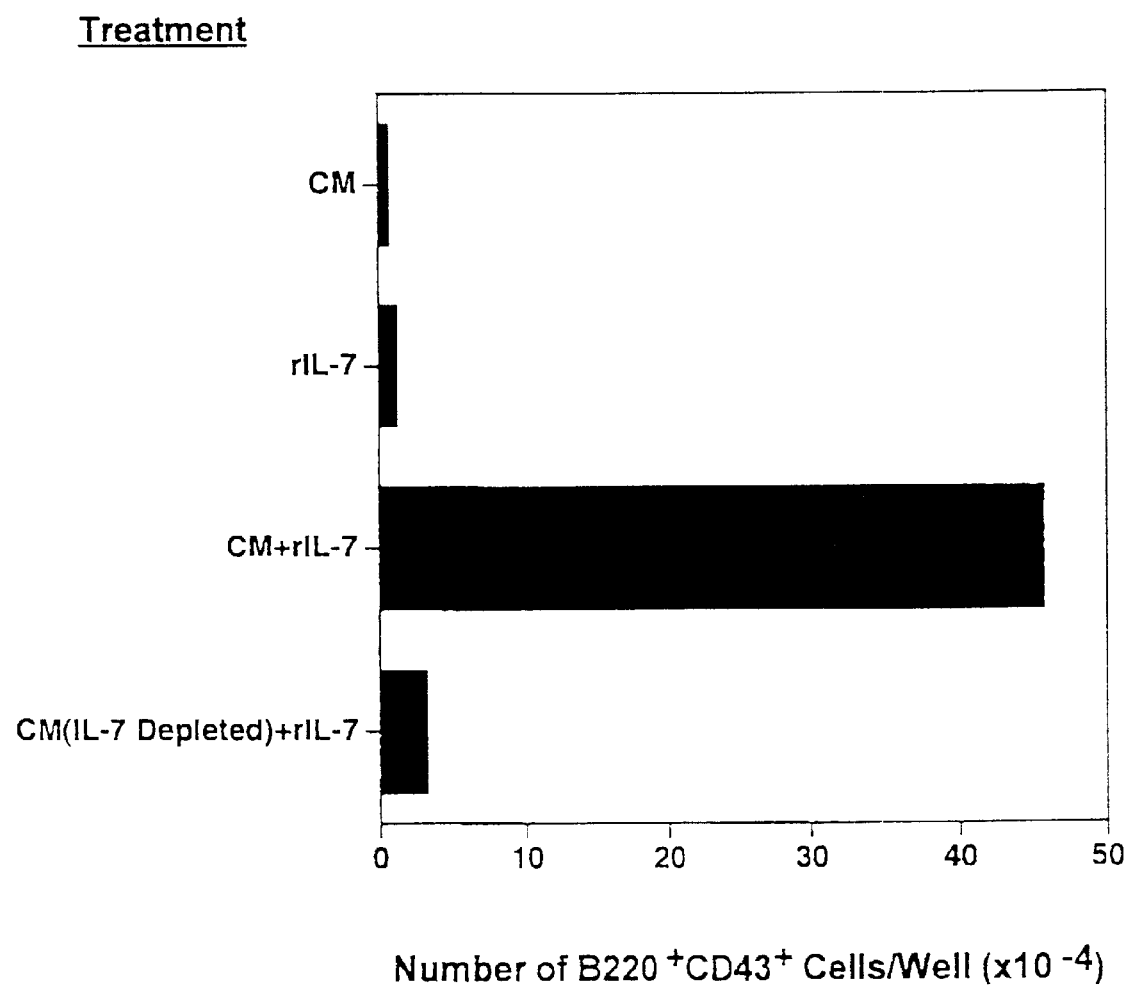
FIG. 27 is a bar graph illustrating that CM plus rIL-7 supports the proliferation of B220$^+$ CD43$^+$ cells from IL-7 KO mice in vitro. 1×10$^6$ BM cells from IL-7 KO mice were incubated for 20 days in medium (RPMI 1640 supplemented with 20% FBS) containing CM from WT BM stromal cells, rIL-7 (10 ng/ml), or both. The CM was either depleted by adsorption with anti-IL-7 mAb or sham-depleted with an isotype control antibody. The cultures were re-fed (50% volume) twice weekly.
Figure 28:
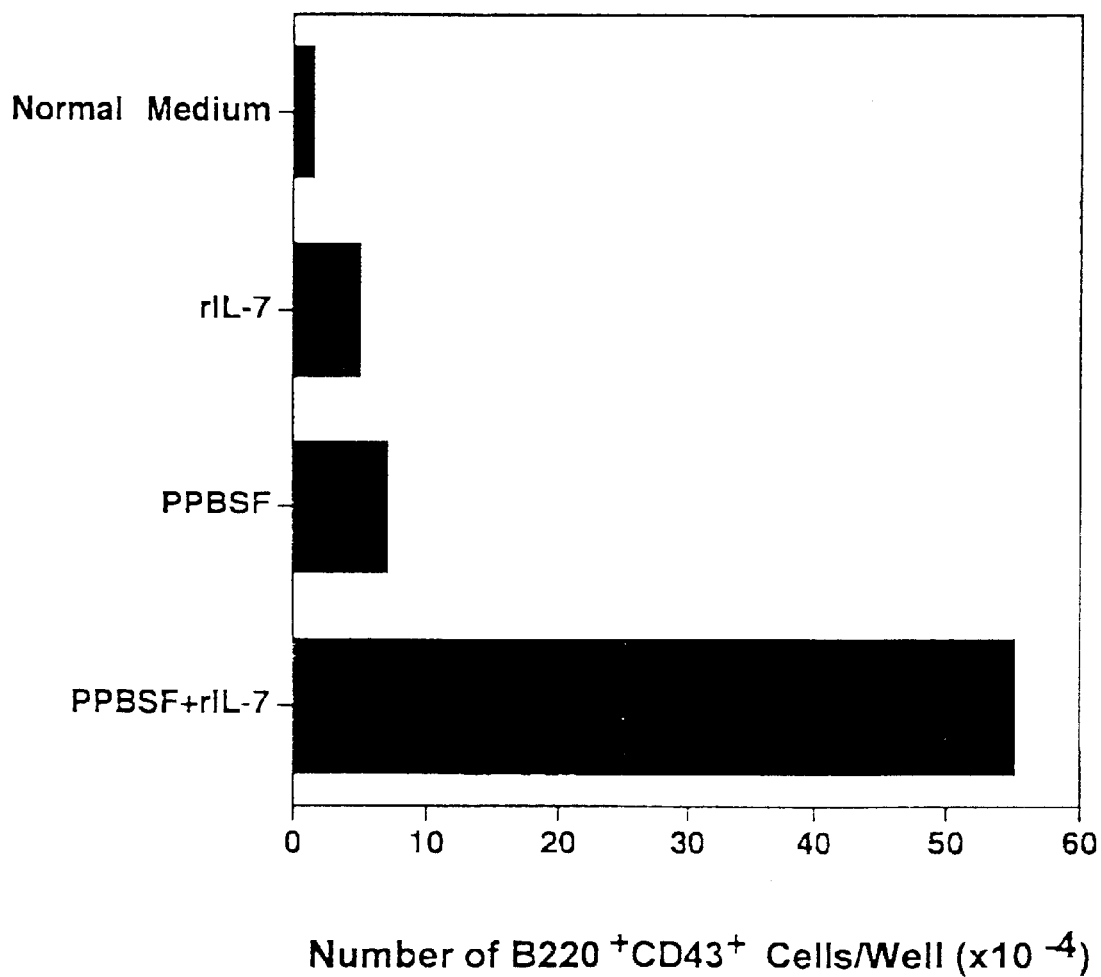
FIG. 28 is a bar graph demonstrating that purified PPBSF plus rIL-7 supports the proliferation of B220$^+$ CD43$^+$ cells from IL-7 KO mice in vitro. 1×10$^6$ BM cells from IL-7 KO mice were incubated for 20 days with medium containing purified PPBSF (10 ng/ml), rIL-7 (10 ng/ml), or both.
Figure 29:
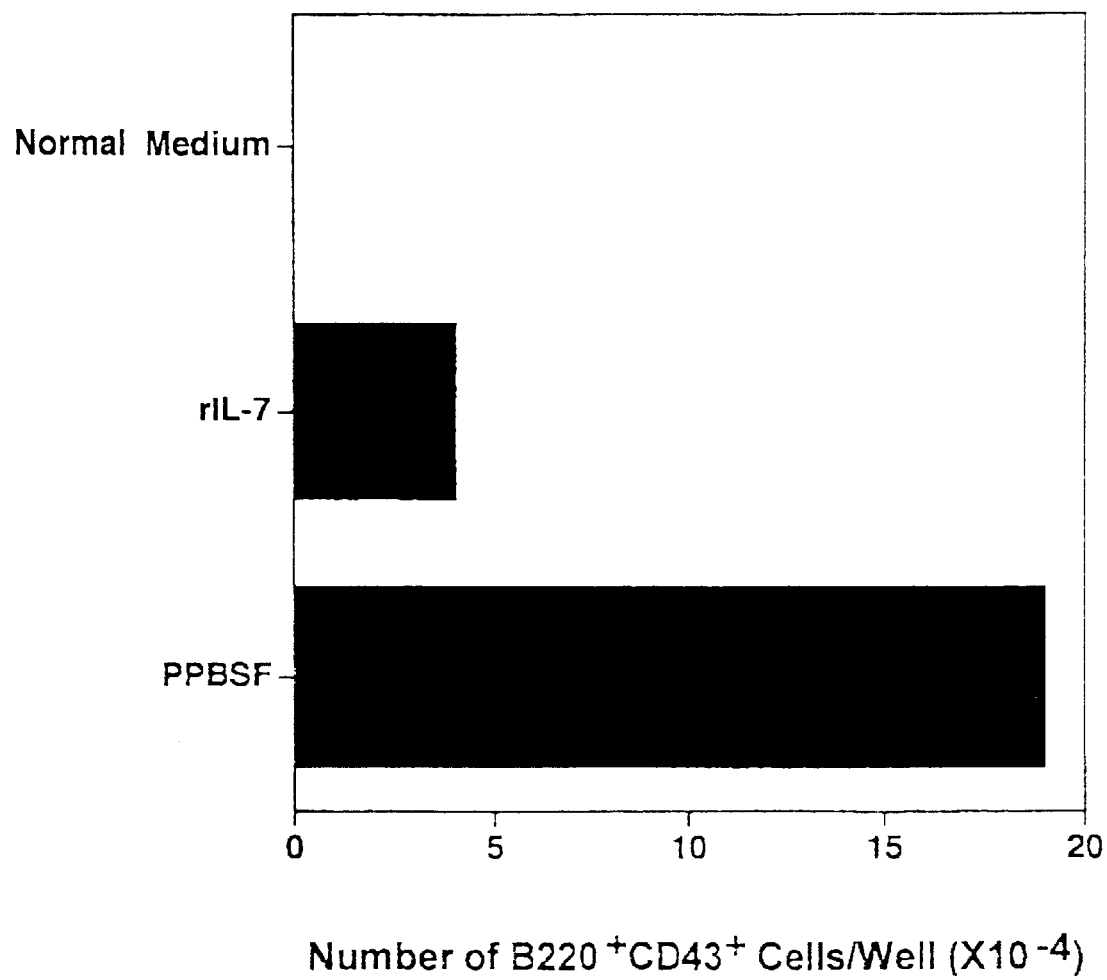
FIG. 29 is a bar graph illustrating the effect of pretreatment in vitro with purified PPBSF, enabling B220$^+$ CD43$^+$ cells from IL-7 KO mice to proliferate in response to rIL-7 alone. 1×10$^6$ BM cells from IL-7 KO mice were incubated for 5 days with medium containing purified PPBSF (10 ng/ml), or rIL-7 (10 ng/ml). The cells from these primary cultures were transferred into secondary cultures and incubated for another 15 days in medium containing rIL-7 only (10 ng/ml).

Similar results were obtained when CM was substituted for the IL-7+/+ stromal cell layers in these cultures (FIG. 27). However, although supplementation with rIL-7 was still required to amplify cell growth, rIL-7 was not able to restore lymphostimulatory activity to CM that had been adsorbed with anti-IL-7 mAb. This observation suggests that the active factor in CM was the heterodimeric form of IL-7, i.e. PPBSF. This was confirmed by demonstrating that purified PPBSF plus rIL-7 could stimulate the in vitro generation of B220$^+$ CD43$^+$ cells (FIG. 28). Furthermore, as shown in FIG. 29, PPBSF and rIL-7 appeared to act sequentially. Thus, when BM cells from IL-7 KO mice were cultured in primary cultures containing PPBSF only, the surviving cells were able to generate B220$^+$ CD43$^+$ cells when transferred to secondary cultures containing rIL-7 only. In contrast, although initial exposure to rIL-7 alone maintained the viability of the B220$^+$ CD43$^+$ cells from IL-7 KO BM, it did not enable these cells to proliferate when restimulated with rIL-7.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety.

We claim:

1. An artificially constructed hybrid cytokine comprising a heterodimer of IL-7 and the β-chain of hepatocyte growth factor (HGF) and further comprising a low molecular weight oligosaccharide linker joining said IL-7 and the β-chain of HGF which cytokine supports the proliferation and differentiation of pre-pro-β-cells.

2. The artificially constructed hybrid cytokine dimer of claim 1 wherein said low molecular weight oligosaccharide is heparin sulfate-derived oligosaccharide.

3. The artificially constructed hybrid cytokine dimer of claim 2 wherein said heparin sulfate-derived oligosaccharide has a molecular weight of less than about 3000 kD.

4. An artificially constructed hybrid cytokine complex comprising the complexed bioactive portions of IL-7 and the β-chain of HGF connected with a flexible linker selected from the group consisting of disulfide bridges, heparin and heparin sulfate derived oligosaccharides, bifunctional and chemical cross-linkers and polypeptide linkers, which cytokine complex supports the proliferation of pre-pro-β-cells wherein said flexible linker is a low molecular weight oligosaccharide.

5. The artificially constructed hybrid cytokine of claim 4 wherein said oligosaccharide is a heparin sulfate-derived oligosaccharide.

6. The artificially constructed hybrid cytokine of claim 5 wherein said heparin sulfate-derived oligosaccharide has a molecular weight of less than about 3000 kD.

7. A biological preparation comprising an artificially constructed hybrid cytokine complex according to claim 4 and a pharmaceutically acceptable carrier.

8. A bimolecular protein complex (IL-7HGFβ) comprising the artificially constructed hybrid cytokine complex according to claim 4 which supports the proliferation and differentiation of pre-pro-β-cells.

9. A bimolecular protein complex (IL-7/HGFβ) according to claim 8 wherein said flexible linker is a low molecular weight oligosaccharide.

10. A bimolecular protein complex (IL-7HGFβ) according to claim 9 wherein said oligosaccharide is a heparin sulfate-derived oligosaccharide.

11. A bimolecular protein complex (IL-7/HGFβ) according to claim 10 wherein said heparin sulfate-derived oligosaccharide has a molecular weight of less than about 3000 kD.

12. A process for producing a hybrid cytokine heterodimer of IL-7 and the β-chain of HGF which comprises
 (a) obtaining recombinantly-derived β-chain of hepatocyte growth factor (HGF) by:
   (1) cloning HGFβ cDNA into mammalian or prokaryotic expression vectors and transfecting or transforming the vectors into mammalian or prokaryotic cells;
   (2) growing the transfected or transformed cells in vitro;
   (3) isolating purified β-chain of hepatocyte growth factor (HGF) by extraction from the cell culture;
 (b) obtaining IL-7 from a recombinant or natural source; and
 (c) linking the recombinantly-derived β-chain of hepatocyte growth factor (HGF) of step (a) with the IL-7 of step (b) by way of a low molecular weight oligosaccharide linker.

* * * * *

UNITED STATES PATENT AND TRADEMARK OFFICE
CERTIFICATE OF CORRECTION

| | | |
|---|---|---|
| PATENT NO. | : 6,749,847 B2 | |
| APPLICATION NO. | : 09/823933 | |
| DATED | : June 15, 2004 | |
| INVENTOR(S) | : Irving Goldschneider and Laijun Lai | |

It is certified that error appears in the above-identified patent and that said Letters Patent is hereby corrected as shown below:

Col. 1

Insert at line 11 -- STATEMENT REGARDING FEDERALLY SPONSORED RESEARCH
    This invention was made with government support under Grant No. AI032752 awarded by the National Institutes of Health (NIH). The government has certain rights in the invention. --

Signed and Sealed this
Thirtieth Day of August, 2011

David J. Kappos
*Director of the United States Patent and Trademark Office*